(12) United States Patent
Wu et al.

(10) Patent No.: US 8,406,848 B2
(45) Date of Patent: Mar. 26, 2013

(54) RECONSTRUCTING THREE-DIMENSIONAL CURRENT SOURCES FROM MAGNETIC SENSOR DATA

(75) Inventors: Chenyu Wu, Mountain View, CA (US); Jing Xiao, Cupertino, CA (US)

(73) Assignee: Seiko Epson Corporation, Tokyo (JP)

( * ) Notice: Subject to any disclaimer, the term of this patent is extended or adjusted under 35 U.S.C. 154(b) by 509 days.

(21) Appl. No.: 12/574,581

(22) Filed: Oct. 6, 2009

(65) Prior Publication Data

US 2011/0081058 A1   Apr. 7, 2011

(51) Int. Cl.
*A61B 5/0484* (2006.01)
(52) U.S. Cl. .................. 600/409; 600/407; 600/544
(58) Field of Classification Search .................. None
See application file for complete search history.

(56) References Cited

U.S. PATENT DOCUMENTS

| | | | |
|---|---|---|---|
| 5,594,849 | A | 1/1997 | Kuc et al. |
| 5,687,737 | A | 11/1997 | Branham et al. |
| 6,456,867 | B2 | 9/2002 | Reisfeld |
| 7,092,748 | B2 | 8/2006 | Valdes Sosa et al. |
| 7,289,843 | B2 | 10/2007 | Beatty et al. |
| 7,333,850 | B2 | 2/2008 | Marossero et al. |
| 2008/0033312 | A1 | 2/2008 | Nakai et al. |

FOREIGN PATENT DOCUMENTS

WO    01/20477 A2    3/2001

OTHER PUBLICATIONS

Baillet et al., Electromagnetic Brain Mapping, Nov. 2001, IEEE Signal Processing Magazine, p. 14-30.*
Marquardt, An algorithm for least-squares estimation of nonlinear parameters, Jun. 1963, J. Soc. Indust. Appl. Math., vol. 11, No. 2.*
Lau et al., Tabu Search Optimization of Magnetic Sensor Systems for Magnetocardiography, Jun. 2008, IEEE Transactions on Magnetics, vol. 44, No. 6, p. 1442-1445.*
Pechenkov, A Mathematical Algorithm for Solving the Inverse Problem of Magnetostatic Flaw Detection, 2005, Russian Journal of Nondestructive Testing, vol. 41, No. 11, 2005, pp. 714-718. Translated from Defektoskopiya, vol. 41, No. 11, 2005, pp. 20-24.*
Jun et al., Fast accurate MEG source localization using a multilayer perceptron trained with real brain noise, Jun. 2002, Physics in Medicine and Biology, 47(14):2547-2560.*
Lau, S., et al., "Strategies for Optimal Design of Biomagnetic Sensor Systems", Sep. 27, 2007.
Fenici, R., "Magnetocardiography provides non-invasive three-dimensional electroanatomical imaging of cardiac electrophysiology", The Anatolian Journal of Cardiology, Jul. 1, 2007.

* cited by examiner

*Primary Examiner* — Long V. Le
*Assistant Examiner* — Bo J Peng

(57) ABSTRACT

Magnetic source imaging (MSI) involves the reconstruction of the current sources in a portion of a body, such as an organ, from measured magnetic field data. The measured magnetic field data may be from one-dimensional or three-dimensional sensors. Aspects of the present invention include systems and methods for reconstructing the electrical current of an organ given magnetic data. In embodiments, reconstruction of three-dimensional current sources is accomplished knowing or estimating the position, or offset, of the sensor plane with respect to the patient in order to form a set of linear equations. Alternatively, reconstruction of three-dimensional current sources is accomplished without knowing the offset of the sensor plane with respect to the patient. In embodiments, the linear and nonlinear systems of equations are iteratively used to obtain the current source information. In embodiments, multi-scale strategies are employed.

20 Claims, 17 Drawing Sheets

500

Represent a portion of a body, such as an organ, as a set of current dipoles within a bounding region wherein each current dipole has a defined position within the bounding region — 505

Represent the magnetic field at a sensor array as a set of non-linear equations of the magnitude and orientation of the set of current dipoles and an offset of the sensor array relative to the bounding region — 510

Simultaneous solve the set of nonlinear equations to obtain the magnitude and orientation of the set of electrical current dipoles and the offset of the sensor array relative to the bounding region — 515

FIGURE 5

RECONSTRUCTING THREE-DIMENSIONAL CURRENT SOURCES FROM MAGNETIC SENSOR DATA

BACKGROUND

A. Technical Field

The present invention pertains generally to data processing, and relates more particularly to obtaining three-dimensional (3D) current from data obtained from an array of magnetic sensors.

B. Background of the Invention

Diagnostic tests are central to patient care. Healthcare professionals need the ability to evaluate patients in order to correctly diagnosis ailments. Diagnostics procedures can be invasive or non-invasive. Because invasive tests carry associated risks, non-invasive diagnostic procedures are often preferred. Non-invasive tests are particularly preferred when investigating critical organs, such as the heart and brain.

One form of non-invasive diagnostic tests is magnetic source imaging. Certain organs of the body, such as the heart and brain, generate currents. These currents arise in the synchronous activity of neurons of the organs, and the electric current produces magnetic fields that extend outside the body. Recording magnetic fields produced by the heart is known as magnetocardiography (MCG), and recording of magnetic fields produced by the brain is known as magnetoencephalography (MEG).

Using these magnetic fields as a diagnostic tool presents challenges. First, although these magnetic fields extend outside the body, they typically are very weak and require extremely sensitive measuring equipment. For example, an array of superconducting quantum interference device (SQUID) detectors can be placed near the organ of interest to detect magnetic fields.

Second, once the measurement data has been taken, the next obstacle is to make the data meaningful. Several prior attempts have made use of such measured data. MCG sensor data has been used to develop two-dimensional (2D) images. Other uses of the data involve displaying magnetic field mapping, which shows the distribution of the magnetic field obtained at specific measurement points and precise moments of time.

Attempts have been made to reconstruct the current distribution of the organ of interest; however, to achieve such a result an inverse problem must be solved. Namely, given the resultant magnetic field, one must attempt to ascertain what system of electrical current sources of the organ produced it. Solving this inverse problem is quite complex, and to reduce this complexity, many prior attempts have simplified the inverse problem in order to reach a result. However, simplifications tend to yield less accurate or in complete results. Accordingly, it is important that magnetic source imaging solutions model the organ as accurately as possible.

SUMMARY OF THE INVENTION

Magnetic source imaging (MSI) involves the reconstruction of the current sources in an organ from measured magnetic field data. The measured magnetic field data may be from one-dimensional or three-dimensional sensors. Aspects of the present invention include systems and methods for reconstructing the electrical current of a portion of the body, such as an organ like the heart or brain, given magnetic data. In embodiments, reconstruction of three-dimensional current sources is accomplished knowing or estimating the position, or offset, of the sensor plane with respect to the patient in order to form a set of linear equations. Alternatively, reconstruction of three-dimensional current sources is accomplished without knowing the offset of the sensor plane with respect to the patient. In embodiments, the linear and nonlinear systems of equations are iteratively used to obtain the current source information. In embodiments, multi-scale strategies are employed.

In embodiments, a method for reconstructing electrical current distribution of a portion of a body comprises representing the portion of the body as a set of electrical current dipoles within a bounding region, each electrical current dipole having a defined position within the bounding region, and representing a magnetic field at a sensor array as a set of linear equations of the magnitude and orientation of the set of electrical current dipoles and a value for the offset between the bounding region and the sensory array. Given the offset, the linear system can be solved to obtain the current information.

In embodiments in which the offset is not known or assumed, the magnetic field in the sensor array is represented as a set of nonlinear equations of the magnitude and orientation of the set of electrical current dipoles and an offset of the sensor array relative to the bounding region. The current dipole information is obtain by setting a value for the offset and using the set of linear equations and the value for the offset to obtain the magnitude and orientation of the set of electrical current dipoles. The electrical current dipoles information obtained from the set of linear equations are input into the set of nonlinear equations to obtain an updated offset. The process is iterated until a stop condition is met.

In embodiments, the stop conditions may include at least one of the following: a difference between the offset and the updated offset is less than a threshold value; a number of iterations have occurred; the solution is diverging; and a measurement reconstruction error is less than a threshold amount.

In embodiments, the set of nonlinear equations is solved using a Levenberg-Marquardt method to obtain the updated offset.

In embodiments, when solving for the updated offset, a parameter is used to help improve convergence to a global optimum value. For example, in embodiments, simulated annealing is used to help the updated value converge to a non-local optimum.

In embodiments, the sensors in the sensor array comprise one-dimensional sensors and the set of the set of nonlinear equations and the set of linear equations each comprises sets of one-dimensional equations.

In embodiments, the electrical current dipole information can be used to model the portion of the body that is under examination. And, in embodiments, the electrical current dipole information of the modeled body may be graphically depicted. In embodiments, the electrical current dipole information may be used to assist in diagnosis and/or treatment.

In embodiments, a multi-scale strategy may be employed in which at an iteration, the number of current dipoles are increased by subdividing at least some of the current dipoles regions. In embodiments, only those regions with a sufficiently strong electrical current are subdivided.

The methods presented herein may be contained in a computer program product comprising at least one computer-readable medium storing one or more sequences of instructions, wherein execution of the one or more sequences of instructions by one or more processors causes the one or more processors to execute a computer-implemented method for reconstructing electrical current distribution of a portion of a body.

Embodiments of the present invention include a computer system or systems for obtaining current information from magnetic data.

Some features and advantages of the invention have been generally described in this summary section; however, additional features, advantages, and embodiments are presented herein or will be apparent to one of ordinary skill in the art in view of the drawings, specification, and claims hereof. Accordingly, it should be understood that the scope of the invention shall not be limited by the particular embodiments disclosed in this summary section.

BRIEF DESCRIPTION OF THE DRAWINGS

Reference will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

FIG. 5 depicts a method for reconstructing electrical current distribution of an organ according to various embodiments of the invention.

DETAILED DESCRIPTION OF THE PREFERRED EMBODIMENTS

Figure 1:
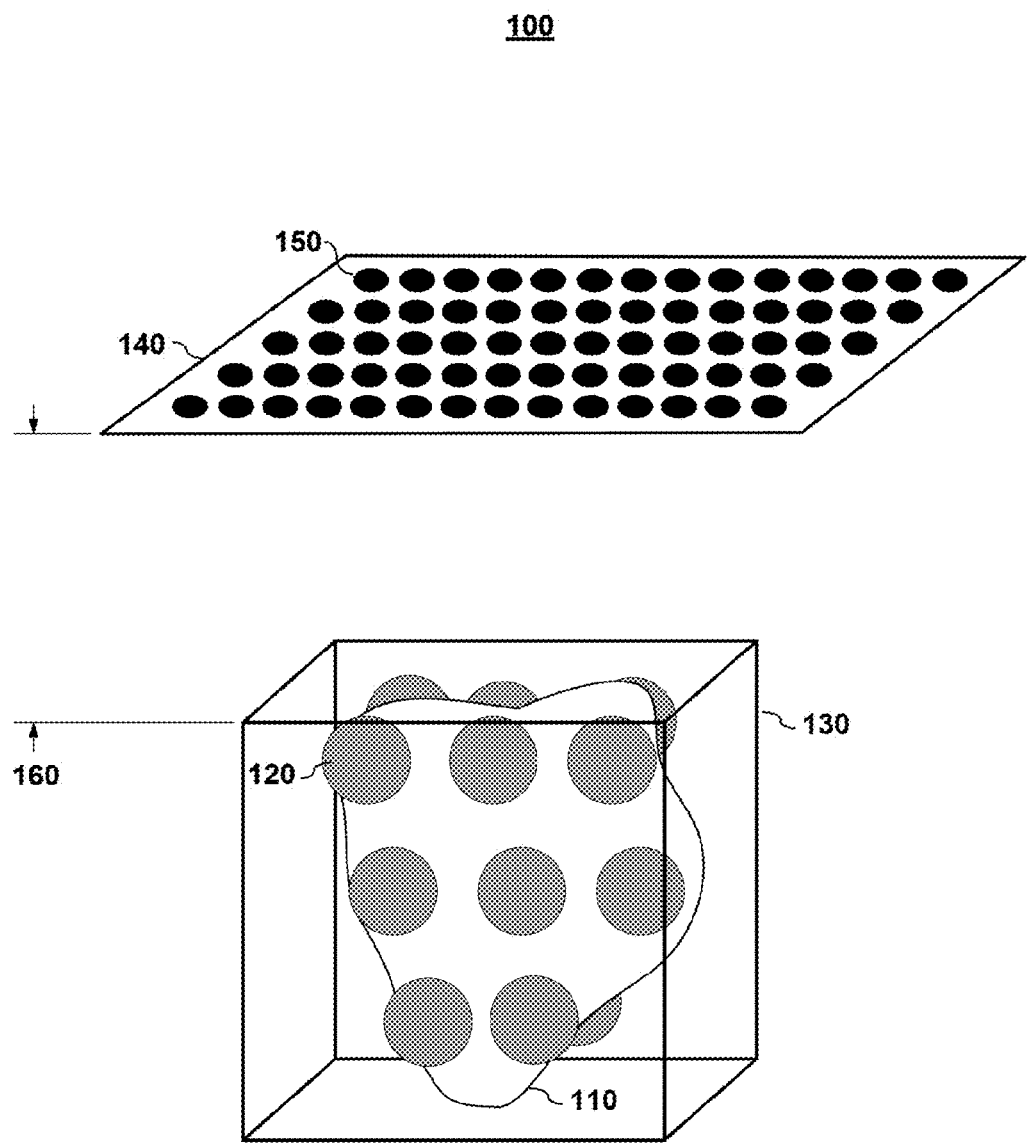
FIG. 1 depicts a sensor array and a heart represented as a three-dimensional volume and a three-dimensional array of current sources, which are used to model the current distribution in the heart, according to various embodiments of the present invention.

In the following description, for purpose of explanation, specific details are set forth in order to provide an understanding of the invention. It will be apparent, however, to one skilled in the art that the invention may be practiced without these details. One skilled in the art will recognize that embodiments of the present invention, some of which are described below, may be incorporated into a number of different systems and devices, including by way of illustration and not limitation, medical diagnostic equipment. Aspects of the present invention may be implemented in software, hardware, firmware, or combinations thereof.

Components, or modules, shown in block diagrams are illustrative of exemplary embodiments of the invention and are meant to avoid obscuring the invention. It shall also be understood that throughout this discussion that components may be described as separate functional units, which may comprise sub-units, but those skilled in the art will recognize that the various components, or portions thereof, may be divided into separate components or may be integrated together, including integrated within a single system or component.

Furthermore, connections between components/modules within the figures are not intended to be limited to direct connections. Rather, data between these components may be modified, re-formatted, or otherwise changed by intermediary components. Also, additional or fewer connections may be used. It shall also be noted that the terms "coupled" or "communicatively coupled" shall be understood to include direct connections, indirect connections through one or more intermediary devices, and wireless connections.

Reference in the specification to "one embodiment," "an embodiment," or "embodiments," means that a particular feature, structure, characteristic, or function described in connection with the embodiment or embodiments is included in at least one embodiment of the invention and may be in more than one embodiment. The appearances of the phrase "in one embodiment," or "in an embodiment," or "in embodiments," in various places in the specification are not necessarily all referring to the same embodiment or embodiments. In systems and methods presented below, it shall be noted that the examination for stop conditions may be skipped for the first (or more) iterations.

A. Overview

Magnetic source imaging (MSI) can involve the reconstruction of the current sources in an organ from measured magnetic field data. That is, magnetic source imaging techniques attempt to obtain the location, orientation, and magnitude of current sources within a body. Two applications of magnetic source imaging are magnetocardiography and magnetoencephalography. Magnetocardiography (MCG) involves a non-invasive and risk-free technique of measuring body-surface recording of the magnetic fields caused by excitement current of the heart. Magnetoencephalography (MEG) involves a non-invasive and risk-free technique of measuring body-surface recording of the magnetic fields caused by excitement current of the brain. Current MCG and MEG systems typically use an ultra-sensitive magnetic sensor (SQUID: super conducting quantum interference device), which enables the non-invasive evaluation of the heart and brain.

Data obtained from these magnetic sensors can be used to model the body part of interest. Modeling the unknown current distribution as one or more current dipoles with unknown position, orientation, and magnitude is vastly complex. Prior attempts to find solution to this inverse problem have involved trying to simplify the model by simplifying the problem in some way. For example, most previous methods only dealt with the two-dimensional current source reconstruction on the surface, and these methods generally model the source as magnetic dipoles instead of current dipoles. To discover the abnormal motion of cardiac muscles or abnormality in some other organ, a solution to a three-dimensional excitement current model is needed.

Other methods have simplified the modeling by eliminating one or more of the unknowns. For example, some methods have fixed the amplitude of each dipole and solved only for location and orientation. Still other methods have treated dipole as a weighted sum of known, elementary sources, which fixes the position of each elementary source and only the amplitude is unknown. An underline assumption of such a model is that these source dipoles are dependent relative to each other. Even with these simplifications, these methods are computationally expensive and are often numerically unstable.

Presented herein are systems and methods to reconstruct a three-dimensional current source. In embodiments, reconstruction of three-dimensional current sources is accomplished without knowing the position, or offset, of the sensor plane with respect to the patient. To develop a real-time system, the current distribution is formulated as an array of current dipoles. The following discussion may use, for purposes of illustration, a heart as the organ of interest that is being investigated; however, it shall be noted that the systems and methods disclosed herein may be used on other portions of the body as well.

B. Initial Setup

FIG. 1 depicts a sensor array 140 and a heart 110 represented as a three-dimensional volume 130 and a three-dimensional array of current sources (e.g., 120), which are used to model the current distribution in the heart 110, according to various embodiments of the present invention. In embodiments, the current dipole sources may be positioned with a defined relationship. For example, the current dipoles may be evenly distributed within the bounding box 130. As shown in FIG. 1, the array of sensors 140 is placed above the heart volume 130 by a three-dimensional offset vector (e.g., 160). After the patient and the device are immobilized, a healthcare professional needs only to position the center of the sensor array approximately over the center of the heart. In embodiments, the present methods and systems automatically estimates the size of the bounding box 130, based on statistics about human heart.

1. Forward Problem at Each Time Instance

Figure 2A:
FIG. 2A depicts a single dipole and a single sensor according to various embodiments of the invention.
Figure 2B:
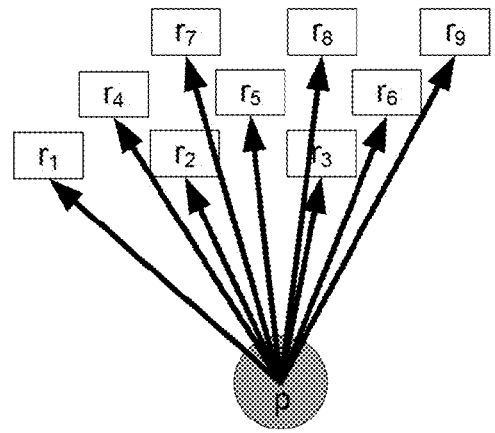
FIG. 2B depicts a single dipole and multiple sensor array according to various embodiments of the invention.
Figure 2C:
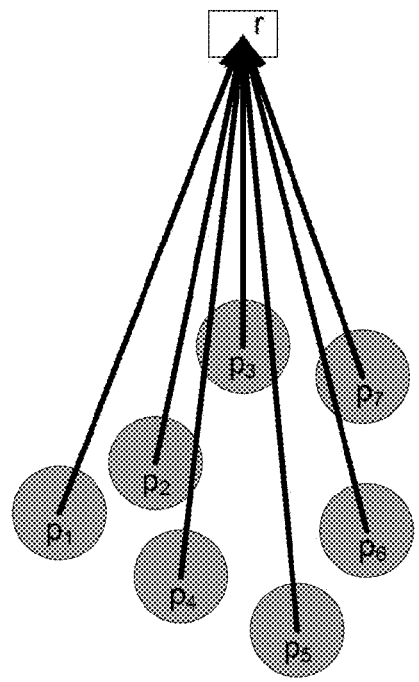
FIG. 2C depicts multiple dipoles and a single sensor according to various embodiments of the invention.

FIGS. 2A-C illustrate the forward problem of electrical dipoles creating magnetic fields. FIG. 2A depicts a single dipole, p, and a single sensor, r. Using the Biot-Savart Law, the magnetic field $\vec{B}(\vec{r})$ at position $\vec{r}$ due to a single current source $\vec{J}(\vec{p})$ is:

$$\vec{B}(\vec{r}) = \frac{\mu_0}{4\pi} \frac{\vec{J}(\vec{p}) \times (\vec{r} - \vec{p})}{\|\vec{r} - \vec{p}\|^3} \quad (1)$$

Although the magnetic field generated by a part of the body, such as the heart, is very weak (typically about $10^{-12} \sim 10^{-11}$ Tesla), it can be detected by sensors at different positions. For example, FIG. 2B depicts a single dipole (p) and a sensor array with multiple sensors ($r_1$-$r_9$) detecting the magnetic field generated by the dipole.

A more accurate representation of a physiological process in an organ, such as the heart, is that many primary current sources exist. Thus, a more accurate model includes multiple dipoles. FIG. 2C depicts multiple dipoles ($p_1$-$p_7$) and a sensor (r) according to various embodiments of the invention. As shown in FIG. 2C, each dipole ($p_1$-$p_7$) contributes to the measured magnetic field at each sensor position (e.g., r).

In embodiments, the problem can be formulated by assuming the current source $\vec{J}(\vec{p})$ at position $\vec{p}$ is independent of the current source $\vec{J}(\vec{p}')$ at position $\vec{p}'$. $\vec{J}(\vec{p})$ is an elementary source, which is different from some prior methods that represent $\vec{J}(\vec{p})$ as a combination of linear bases. In embodiments of the modeling, there are n dipoles at different positions, $q_n$ represents the magnitude of each dipole, and $\vec{J}$ is a unit vector. Thus, the positions of the dipoles are fixed relative to each other, but the magnitude and direction of each dipole are unknown. Extending Equation (1) to multiple dipoles yields the following equation:

$$\vec{B}(\vec{r}) = \frac{\mu_0}{4\pi} \sum_{n=1}^{N} \frac{q_n \vec{J}(\vec{p_n}) \times (\vec{r} - \vec{p_n})}{\|\vec{r} - \vec{p_n}\|^3} \quad (2)$$

An array of M sensors yields the following set of equations:

$$\vec{B}(\vec{r_m}) = \frac{\mu_0}{4\pi} \sum_{n=1}^{N} \frac{q_n \vec{J}(\vec{p_n}) \times (\vec{r_m} - \vec{p_n})}{\|\vec{r_m} - \vec{p_n}\|^3}, m = 1 \ldots M \quad (3)$$

where $\vec{p_n}$ is the three-dimensional position of the $n^{th}$ dipole, and $\vec{r_m}$ is the three-dimensional position of the $m^{th}$ sensor.

2. Inverse Problem Solution Embodiments

In some prior methods, the forward problem was simplified into a set of linear equations and the solution is the inverse of the linear equations. In embodiments, the offset can also be treated as an unknown and a set of nonlinear equations will be solved.

Presented below are two general approaches to solving the inverse problem. The first approach deals with situations in which the offset between the sensor array and the bounding box is known. Because a correct offset is not always available, the second approach addresses unknown offset.

a) Closed Form Solutions Given Offset

Given a fixed configuration of dipoles $\vec{p_n}$ and a known configuration of sensors $\vec{r_m}$, Equation (3) may be written as:

$$\vec{B}_m = \sum_{n=1}^{N} \vec{J}_n \times \vec{R}_{mn} = -\sum_{n=1}^{N} \vec{R}_{mn} \times \vec{J}_n, \quad (4)$$

where $$\vec{B}_m = \vec{B}_m(\vec{r}_m), \vec{J}_n = q_n \vec{J}(\vec{p}_n),$$

and $$\vec{R}_{mn} = \frac{\mu_0}{4\pi} \frac{(\vec{r}_m - \vec{p}_n)}{\|\vec{r}_m - \vec{p}_n\|^3}.$$

$\vec{B}_m$ values are measured, $\vec{R}_{mn}$ values are computed, and $\vec{J}_n$ are unknowns. Equations (4) can be expanded to a matrix form by using skew-symmetric matrix.

$$\vec{B}_m = -\sum_{n=1}^{N} [\vec{R}_{mn}] \times \vec{J}_n = -\sum_{n=1}^{N} \begin{bmatrix} 0 & -R_{mn}^3 & R_{mn}^2 \\ R_{mn}^3 & 0 & -R_{mn}^1 \\ R_{mn}^2 & R_{mn}^1 & 0 \end{bmatrix} \begin{bmatrix} J_n^1 \\ J_n^2 \\ J_n^3 \end{bmatrix} \quad (5)$$

Rewriting the equation to remove the summation notation, the equation can be expressed as follows:

$$\begin{bmatrix} B_m^1 \\ B_m^2 \\ B_m^3 \end{bmatrix} = \begin{bmatrix} 0 & R_{m1}^3 & -R_{m1}^2 & |...| & 0 & R_{mN}^3 & -R_{mN}^2 \\ -R_{m1}^3 & 0 & R_{m1}^1 & |...| & -R_{mN}^3 & 0 & R_{mN}^1 \\ R_{m1}^2 & -R_{m1}^1 & 0 & |...| & R_{mN}^2 & -R_{mN}^1 & 0 \end{bmatrix} \begin{bmatrix} J_1^1 \\ J_1^2 \\ J_1^3 \\ \vdots \\ J_N^1 \\ J_N^2 \\ J_N^3 \end{bmatrix} \quad (6)$$

Given M sensors, the following linear system is obtained:

$$\underbrace{\begin{bmatrix} B_1^1 \\ B_1^2 \\ B_1^3 \\ \vdots \\ B_M^1 \\ B_M^2 \\ B_M^3 \end{bmatrix}}_{B} = \underbrace{\begin{bmatrix} 0 & R_{11}^3 & -R_{11}^2 & |...| & 0 & R_{1N}^3 & -R_{1N}^2 \\ -R_{11}^3 & 0 & -R_{11}^1 & |...| & -R_{1N}^3 & 0 & R_{1N}^1 \\ R_{11}^2 & -R_{11}^1 & 0 & |...| & R_{1N}^2 & -R_{1N}^1 & 0 \\ - & - & - & |...| & - & - & - \\ \vdots & & & |...| & & & \vdots \\ - & - & - & |...| & - & - & - \\ 0 & R_{m1}^3 & -R_{M1}^2 & |...| & 0 & R_{MN}^3 & -R_{MN}^2 \\ -R_{M1}^3 & 0 & R_{M1}^1 & |...| & -R_{MN}^3 & 0 & R_{MN}^1 \\ R_{M1}^2 & -R_{M1}^1 & 0 & |...| & R_{MN}^2 & -R_{MN}^1 & 0 \end{bmatrix}}_{R} \underbrace{\begin{bmatrix} J_1^1 \\ J_1^2 \\ J_1^3 \\ \vdots \\ J_N^1 \\ J_N^2 \\ J_N^3 \end{bmatrix}}_{J} \quad (7)$$

where B is a 3M×1 vector, R is a 3M×3N vector matrix, and J is a 3N×1 vector. When rank(R)≧3N, a least square solution can be used to solve for J:

$$J = (R^T R)^{-1} R^T B \quad (8)$$

Figure 3A:
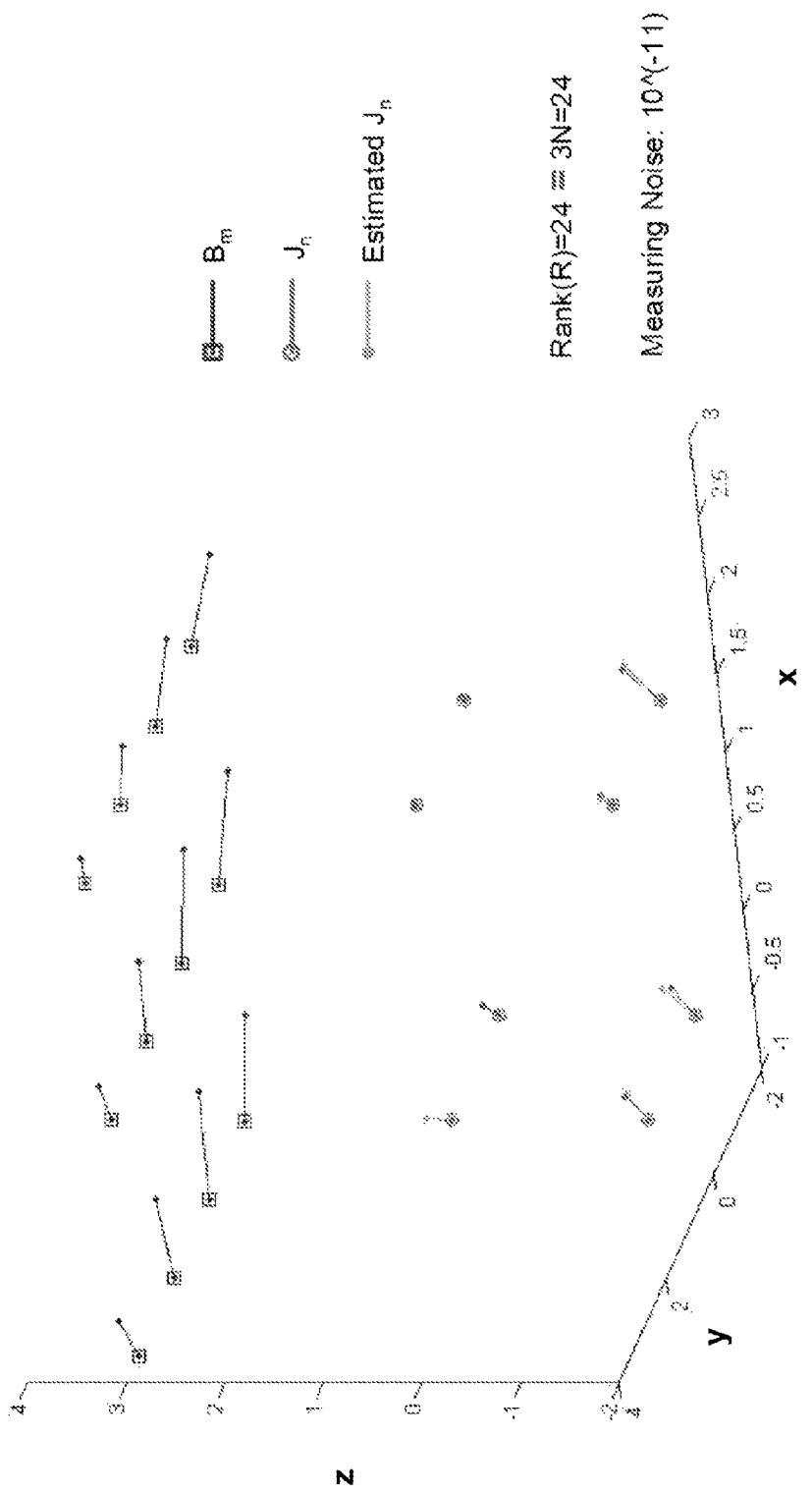
FIG. 3A illustrates simulated results obtained according to various embodiments of the invention.
Figure 3B:
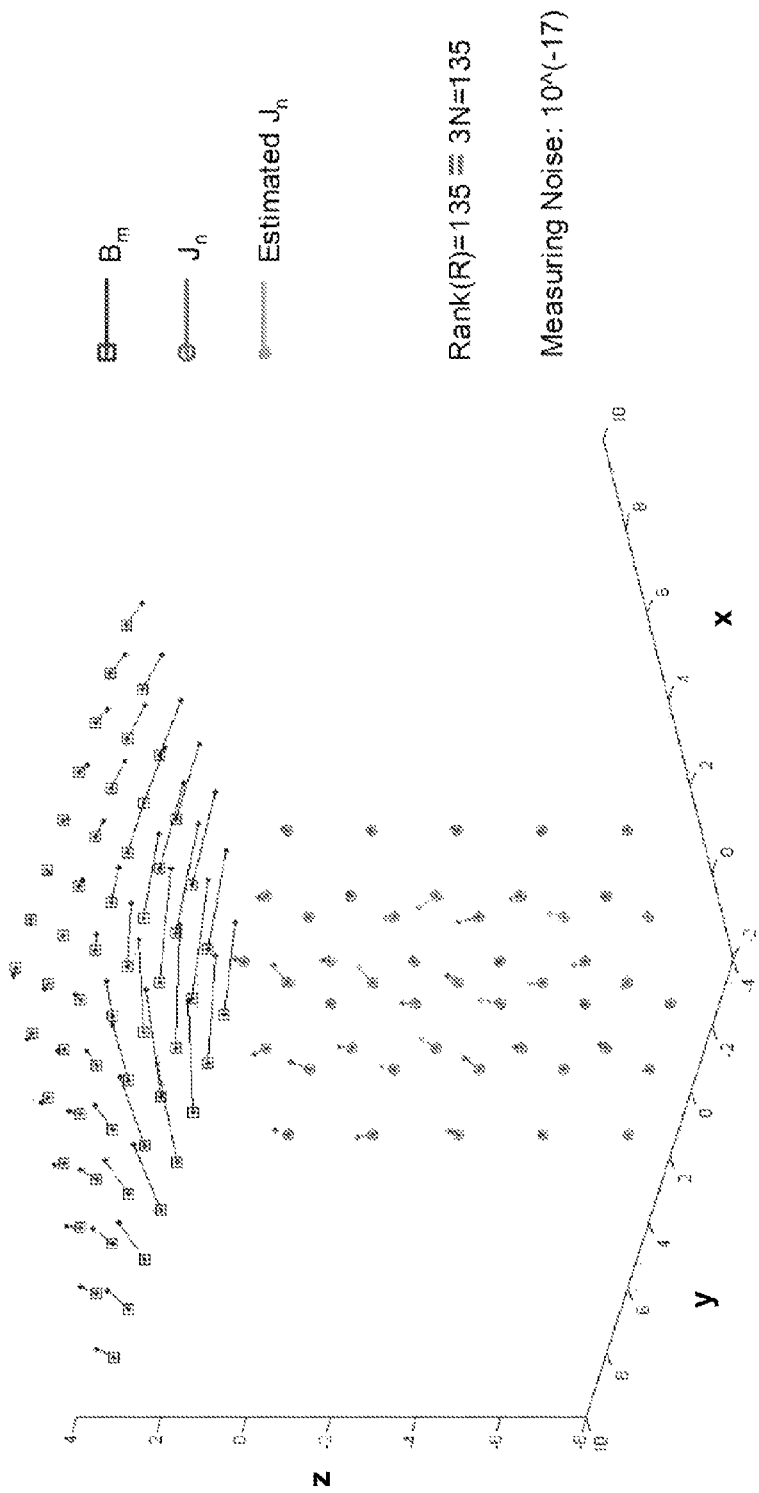
FIG. 3B illustrates simulated results obtained according to various embodiments of the invention.
Figure 3C:
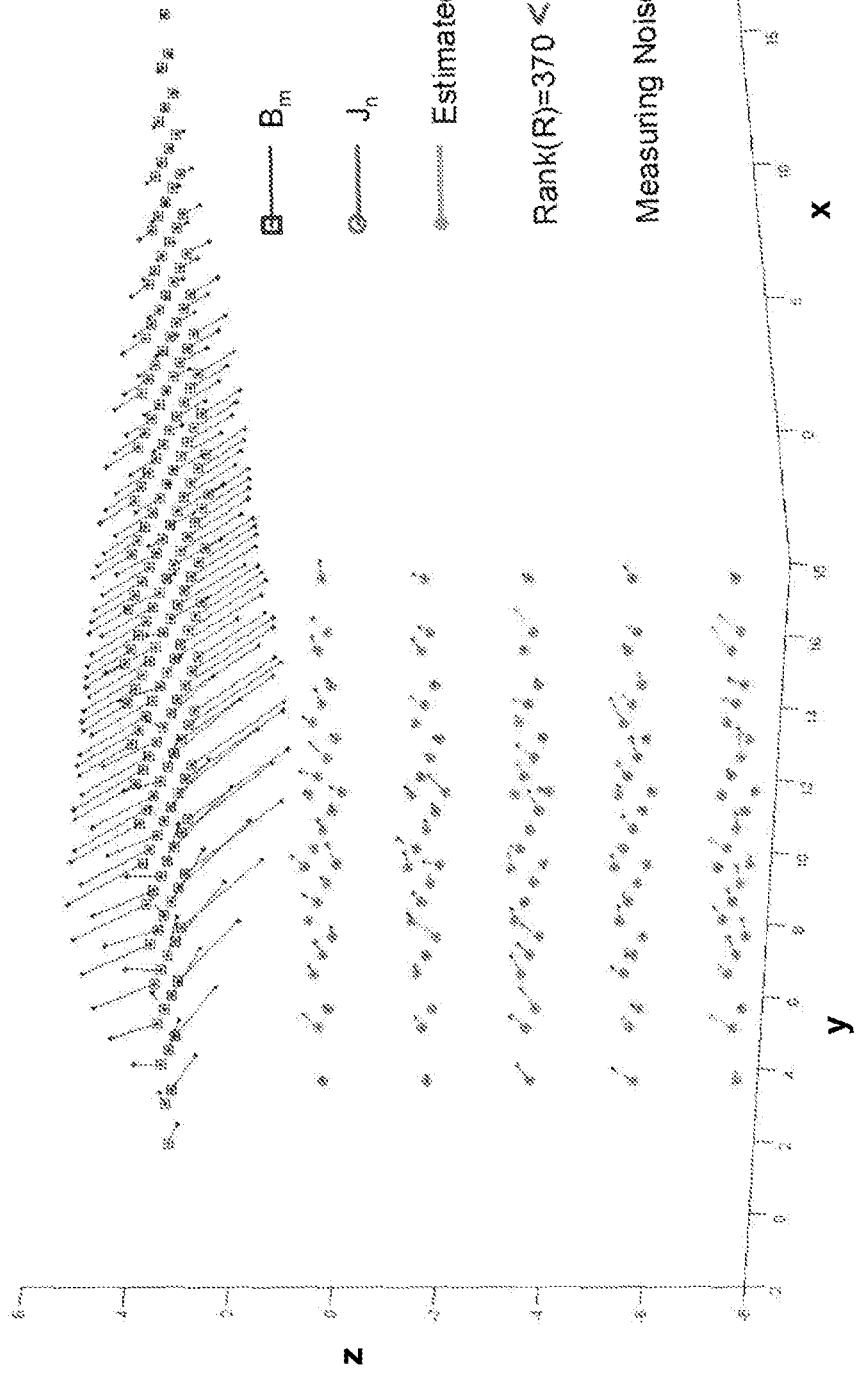
FIG. 3C illustrates simulated results obtained according to various embodiments of the invention.

FIGS. 3A-3C depict some simulation results. In the case depicted in FIG. 3A, where the rank(R)=3N, it can be seen that the reconstruction error is still small when the magnitude of measuring noise is in the level of $10^{-11}$. It should also be noted that increasing the size of the sensor array can make the solution more stable. On the other hand, the reconstruction error appears to be more sensitive to the measuring noise when increasing the size of the current array. Consider, for example, the simulated results depicted in FIG. 3B. In the case depicted in FIG. 3B, where the rank(R)=3N, it can be seen that the reconstruction is more sensitive to the measuring noise ($10^{-17}$) when increasing the size of current array. Additionally, it should be noted that the position of the sensor array affects the solution even with a known offset. Consider, for example, the simulated results depicted in FIG. 3C. In FIG. 3C, the center of the sensor array is far away from the center axis of the current array. In the depict results, the measuring noise is at a level of $10^{-19}$ but the rank(R)<3N, because of the position of the sensor array. Because of the large displacement, most of the sensors that are far away from the current array cannot detect a magnetic field. As a result, there are effectively fewer sensors that can be used to compute a solution to the inverse problem.

b) Solutions Without Offset

Without knowing the value of the offset ($\vec{\epsilon}_0$) between the sensor array and the organ under examination, R is unknown. This unknown offset makes solving the inverse problem difficult.

Figure 4:
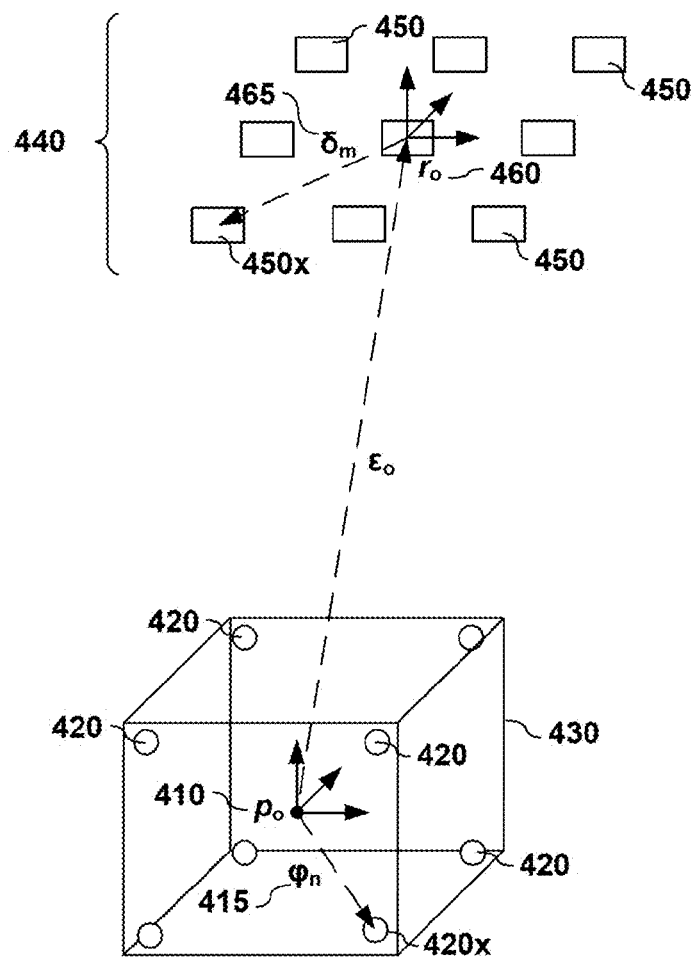
FIG. 4 depicts the unknown position vectors of dipoles relative to the sensor array according to various embodiments of the invention.

Consider the constraints depicted in FIG. 4. FIG. 4 illustrates the unknown position vectors between the sensors and the current dipoles according to various embodiments of the invention. Depicted in FIG. 4 is a bounding region 430 within which are a plurality of current dipoles 420, which are graphically represented by circles (not all dipoles are labeled in order to simply the figure), that have fixed relationship to each other. Also depicted in FIG. 4 is an array 440 of sensors 450, which are graphically represented by rectangles (not all sensors are labeled in order to simply the figure), that have fixed relationship to each other. The current dipole configuration has an origin point, $p_0$ 410, and the sensor array also has an origin point, $r_0$ 460. Because the displacement ($\vec{\delta}_m$) between the sensor origin point, $r_0$, and each sensor 450x is known, and because the displacement ($\vec{\phi}_n$) between the current dipole array origin point, $p_0$, and each sensor 420x is known, the position of any source dipole can be expressed as:

$$\vec{p}_n = \vec{p}_0 + \vec{\phi}_n$$

and the position of any sensor can be expressed as:

$$\vec{r}_m = \vec{r}_0 + \vec{\delta}_m$$

Furthermore, the displacement, or offset ($\vec{\epsilon}_0$), can be used to relate the position of the current dipole array origin point, $p_0$, to the sensor origin point, $r_0$, as expressed below:

$$\vec{r}_0 = \vec{p}_0 + \vec{\epsilon}_0$$

Both the current dipole array origin point ($\vec{p}_0$) and the offset ($\vec{\epsilon}_0$) are unknown. The position of the current dipole array origin point ($\vec{p}_0$) can be set as the global coordinates such that only the offset ($\vec{\epsilon}_0$) is the only unknown. For example, in embodiments, the current dipole array origin point ($\vec{p}_0$) can be set at the center of the bounding box.

Equation (3) can then be rewritten as follows:

$$\vec{B}_m = \frac{\mu_0}{4\pi} \sum_{n=1}^{N} \frac{\vec{J}_n \times ((\vec{r}_0 + \vec{\delta}_m) - (\vec{p}_0 + \vec{\varphi}_n))}{\|(\vec{r}_0 + \vec{\delta}_m) - (\vec{p}_0 + \vec{\varphi}_n)\|^3} \quad (9)$$

-continued $$= \frac{\mu_o}{4\pi} \sum_{n=1}^{N} \frac{\vec{J}_n \times (\vec{\varepsilon}_0 + \vec{\delta}_m - \vec{\varphi}_n)}{\|\vec{\varepsilon}_0 + \vec{\delta}_m - \vec{\varphi}_n\|^3}$$

Let $$\alpha = \frac{4\pi}{\mu_o}$$

and let $\vec{\gamma}_{mn} = \vec{\delta}_m - \vec{\varphi}_n$, which is known and fixed. Then, Equation (9) can be rewritten as follows:

$$\alpha \vec{B}_m = \sum_{n=1}^{N} \frac{\vec{J}_n \times (\vec{\varepsilon}_0 + \vec{\gamma}_{mn})}{\|\vec{\varepsilon}_0 + \vec{\gamma}_{mn}\|^3} \quad (10)$$

$$= \sum_{n=1}^{N} \frac{\vec{J}_n \times \vec{\varepsilon}_0 + \vec{J}_n \times \vec{\gamma}_{mn}}{\|\vec{\varepsilon}_0 + \vec{\gamma}_{mn}\|^3}$$

Let $\vec{\tau}_{mn} = \vec{J}_n \times \vec{\gamma}_{mn}$ and let $\vec{\varepsilon}_0 = (x, y, z)^T$.

$\vec{\tau}_{mn}$ can be computed given $\vec{J}_n$. Removing the cross product by using skew-symmetric matrix yields the following equation:

$$\alpha \vec{B}_m = \sum_{n=1}^{N} \frac{\begin{bmatrix} 0 & -J_n^3 & J_n^2 \\ J_n^3 & 0 & -J_n^1 \\ -J_n^2 & J_n^1 & 0 \end{bmatrix} \begin{bmatrix} x \\ y \\ z \end{bmatrix} + \begin{bmatrix} \tau_{mn}^1 \\ \tau_{mn}^2 \\ \tau_{mn}^3 \end{bmatrix}}{((x + \gamma_{mn}^1)^2 + (y + \gamma_{mn}^2)^2 + (z + \gamma_{mn}^3)^2)^{3/2}} \quad (11)$$

Thus for each m=1:M, three nonlinear equations are obtained in terms of (x, y, z), as depicted below:

$$f_m^1(x, y, z) = -\alpha B_m^1 + \sum_{n=1}^{N} \frac{-J_n^3 y + J_n^2 z + \tau_{mn}^1}{((x + \gamma_{mn}^1)^2 + (y + \gamma_{mn}^2)^2 + (z + \gamma_{mn}^3)^2)^{3/2}} = 0$$

$$f_m^2(x, y, z) = -\alpha B_m^2 + \sum_{n=1}^{N} \frac{-J_n^3 x + J_n^1 z + \tau_{mn}^2}{((x + \gamma_{mn}^1)^2 + (y + \gamma_{mn}^2)^2 + (z + \gamma_{mn}^3)^2)^{3/2}} = 0$$

$$f_m^3(x, y, z) = -\alpha B_m^3 + \sum_{n=1}^{N} \frac{-J_n^2 x + J_n^1 y + \tau_{mn}^3}{((x + \gamma_{mn}^1)^2 + (y + \gamma_{mn}^2)^2 + (z + \gamma_{mn}^3)^2)^{3/2}} = 0$$

Let $F_m = (f_m^1, f_m^2, f_m^3)^T = 0$ and $F = (F_1^T, F_2^T, \ldots, F_M^T)^T = 0$. The nonlinear system F can be solved to obtain a least square solution.

(i) Solving the Nonlinear System Simultaneously

FIG. 5 depicts a method for reconstructing electrical current distribution of an organ according to various embodiments of the invention. In embodiment, the organ under examination is represented (505) as a set of current dipoles within a bounding region wherein each current dipole has a defined position within the bounding region. For example, in embodiments, the current dipoles may be evenly distributed within the bounding box, although one skilled in the art shall recognize that other distributions may be used. The magnetic field at a sensor array that detects the magnetic field caused by the electrical currents in the organ is represented (510) as a set of nonlinear equations of the magnitude and orientation of the set of current dipoles and an offset of the sensor array relative to the bounding region. The nonlinear system of Equation (12) (above) is an embodiment of such a nonlinear system. The nonlinear system of equations of Equation (12) can be simultaneously solved to obtain the magnitude and orientation of the set of electrical current dipoles and the offset of the sensor array relative to the bounding region. When $\vec{J}_n$ is unknown, $\gamma_{mn}$ is also unknown, a Levenberg-Marquardt optimization may be used to solve all these unknowns.

(ii) Solving the Nonlinear System Using Iteration

In embodiments, to address the issue of unknown offset, dual update methodology may be employed. In embodiments, a dual update method may iterate between a linear system (such as, by way of example and not limitation, Equation (8)) and a nonlinear system (such as, by way of example and not limitation, Equation (12)).

Figure 6:
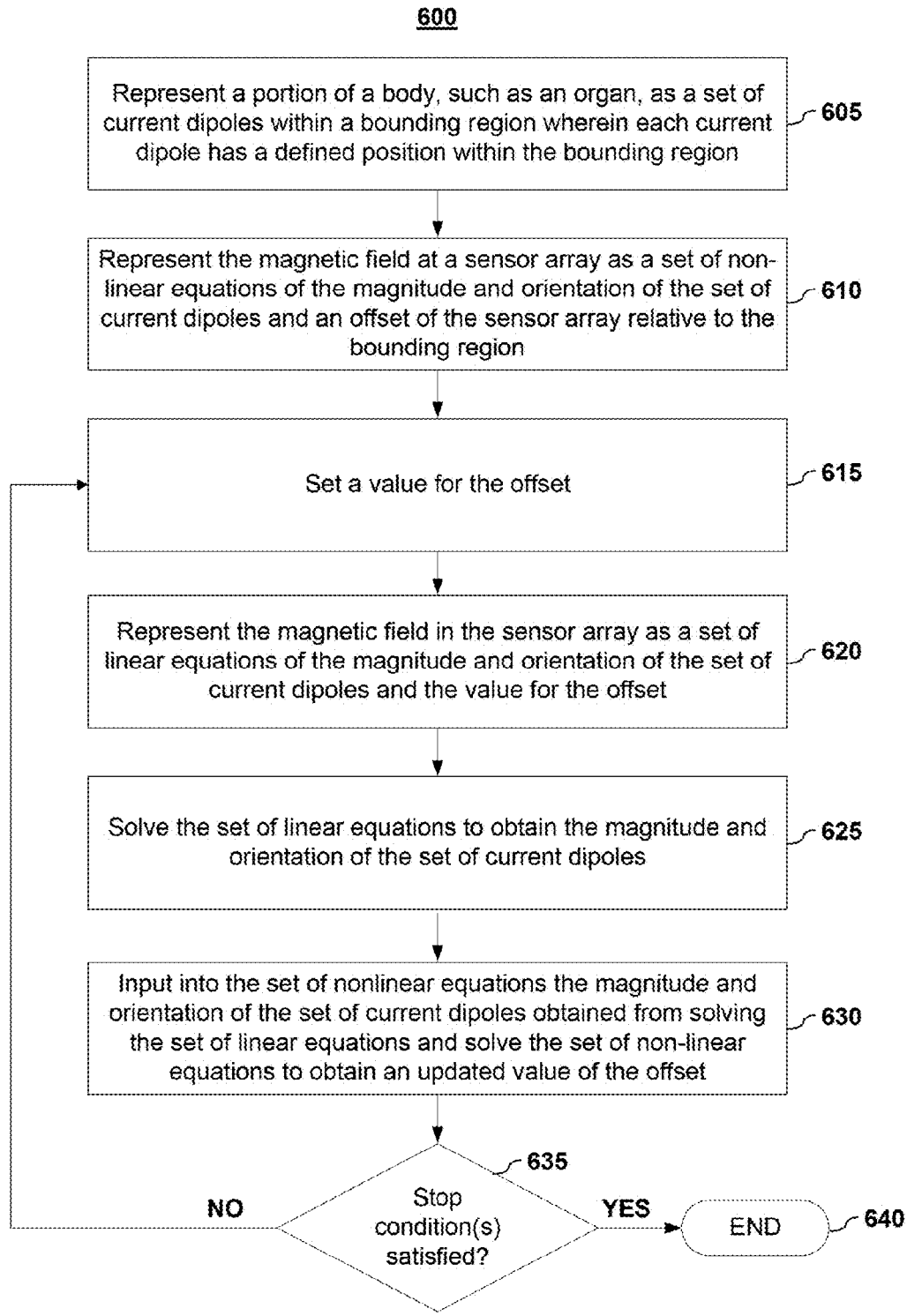
FIG. 6 depicts an alternative method for reconstructing electrical current distribution of an organ according to various embodiments of the invention.

FIG. 6 depicts a method for reconstructing electrical current distribution of an organ by iterating using a linear system and a nonlinear system according to various embodiments of the invention. As with the prior method, the body part of interest is represented (605) as a set of current dipoles within a bounding region wherein each current dipole has a defined position within the bounding region. And, the magnetic field at a sensor array is expressed (610) as a set of nonlinear equations of the magnitude and orientation of the set of current dipoles and an offset of the sensor array relative to the bounding region, such as Equation (12) (above). A value for the offset is selected (615). In embodiments, the initial value for the offset may be an estimate. The estimate may be based upon statistical data of anatomy, measurements taken of the patient, measurements of the equipment configuration, measurements of the set-up, or combinations thereof.

As was noted previously, the magnetic field in the sensor array can be represented (620) as a set of linear equations of the magnitude and orientation of the set of current dipoles and the value for the offset. For example, Equation (8) sets forth a (12)

linear system to obtain the current source, J. Thus, the set of linear equations can be solved (625) to obtain the magnitude and orientation of the set of current dipoles. Equation (8) sets forth a least squared solution to the linear system.

The magnitude and orientation of the set of current dipoles obtained from the set of linear equations can be inputted (630) into the set of nonlinear equations. The set of nonlinear equations can be solved to obtain an update value of the offset. In embodiments, a Levenberg-Marquardt optimization may be employed to obtain a solution.

In embodiments, if a stop condition is satisfied (635), the method stops (640). Stop conditions may include, but are not limited to: (1) the difference between the prior offset value and the updated value of the offset are within a threshold value; (2) a set number of iterations have occurred; (3) the solution appears to be diverging; and (4) the measurement reconstruction error is smaller than a threshold value. If a stop condition has not been satisfied (635), the method iterates in which the updated value of the offset is used as the value of the offset (Step 615) for the next iteration. That is, once an offset ($\vec{\epsilon}_0$) is obtained, the position of the sensors can be estimated and J can be computed again. This process is iterated until the algorithm converges as depicted in FIG. 7.

Figure 7:
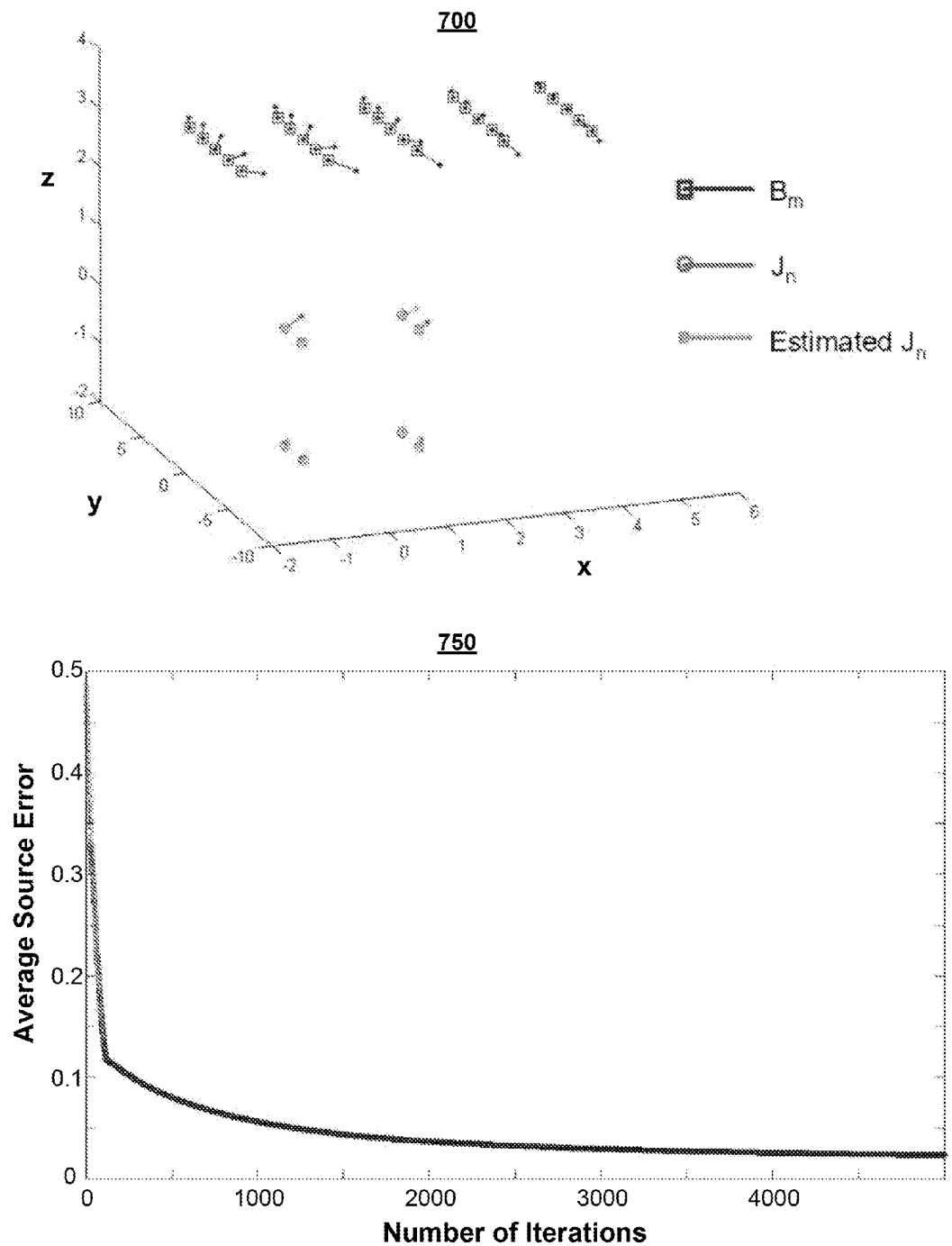
FIG. 7 illustrates simulated results and the associated error obtained according to various embodiments of the invention.

FIG. 7 illustrates simulated results and the associated error obtained according to various embodiments of the invention. Graph 700 depicts magnetic fields at the sensor array and the corresponding current dipoles. Graph 750 depicts the error versus the number of iterations. In the simulated results depicted in FIG. 7, the error decreases below 0.025 after 5000 iterations.

It should be noted that in some cases the error may not be monotonically decreasing along iterations. Thus, in embodiments, strategies may be employed to avoid a local optimum. In embodiments, a good initial start will likely lead to the global optimum; however, it is not always possible to have a correct initial estimate.

One strategy to avoid a local optimum, once an optimum is reached, is to search the neighborhood of the optimum to see if there is a better solution than the current optimum. In embodiment, searching the neighborhood may involve randomly moving away from the current optimum and iterating to see if a better solution is found. Once an optimum is reached and the neighborhood searched, if better results are not found within a set number of iterations, then the initial optimum is retained as the solution.

Figure 8:
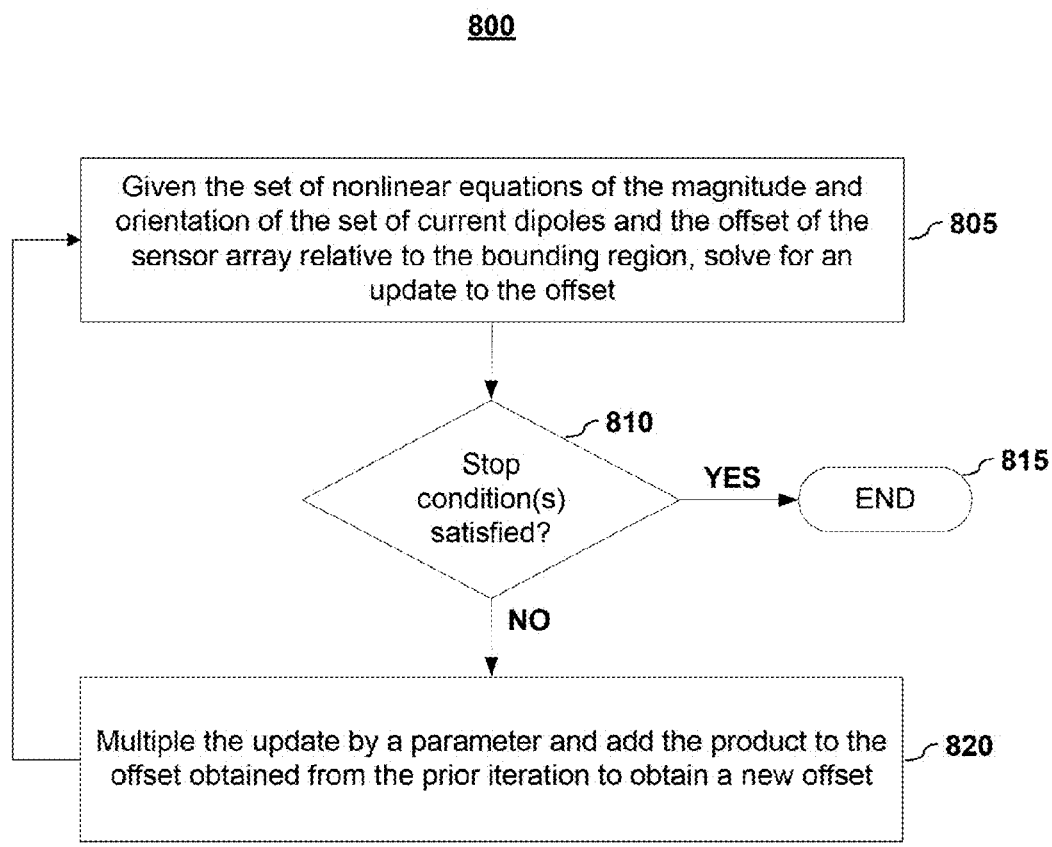
FIG. 8 depicts an aspect of methods for reconstructing electrical current distribution of an organ in order to improve convergence upon a solution according to various embodiments of the invention.

FIG. 8 depicts an aspect of methods for reconstructing electrical current distribution of an organ in order to improve convergence upon a solution according to various embodiments of the invention. In embodiment, given a nonlinear system, such as the system illustrated by Equation (12), a Levenberg-Marquardt method may be used to solve (805) for the offset. The Levenberg-Marquardt method can be considered as a combination of gradient decent and Quasi-Newton methods. This method iteratively updates the offset, $\vec{\epsilon}_0$. In each iteration, the Levenberg-Marquardt method finds a small change, $\Delta \vec{\epsilon}_0$, and the new offset is computed by adding this small change to the offset obtained from the last iteration, i.e., $\vec{\epsilon}_0^{i+1} = \vec{\epsilon}_0^i + \Delta \vec{\epsilon}_0$. Introducing a parameter and multiplying (820) the parameter to the change of the offset in each iteration, i.e. $\vec{\epsilon}_0^{i+1} = \vec{\epsilon}_0^i + T\Delta \vec{\epsilon}_0$, where T is the parameter, can improve convergence to a global optimum. In embodiments, T will decrease over the iterations when the residual of the cost function of nonlinear system decreases. In embodiments, the parameter is decreased automatically. For example, in embodiments, T is initialized to a value and is decreased by 50% whenever the measurement reconstructed error decreases by 10%. One skilled in the art shall recognize that other percentage may be used. By this means, in the first several iterations, the change of the offset can by big enough to avoid local minimum. When the offset is close to the true value, the parameter will decrease and the change of the offset will be small to reach the solution. Those skilled in the art shall recognize the above as an implementation of simulated annealing, in which T is a temperature parameter.

Figure 9A:
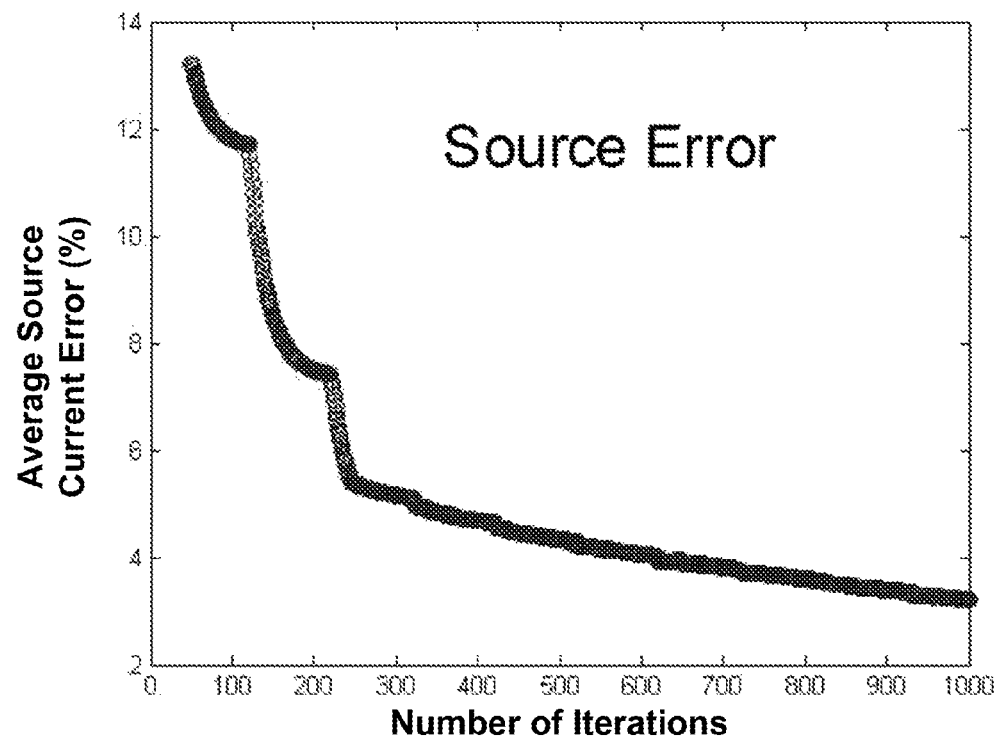
FIG. 9A depicts the estimated current source error according to various embodiments of the invention.
Figure 9B:
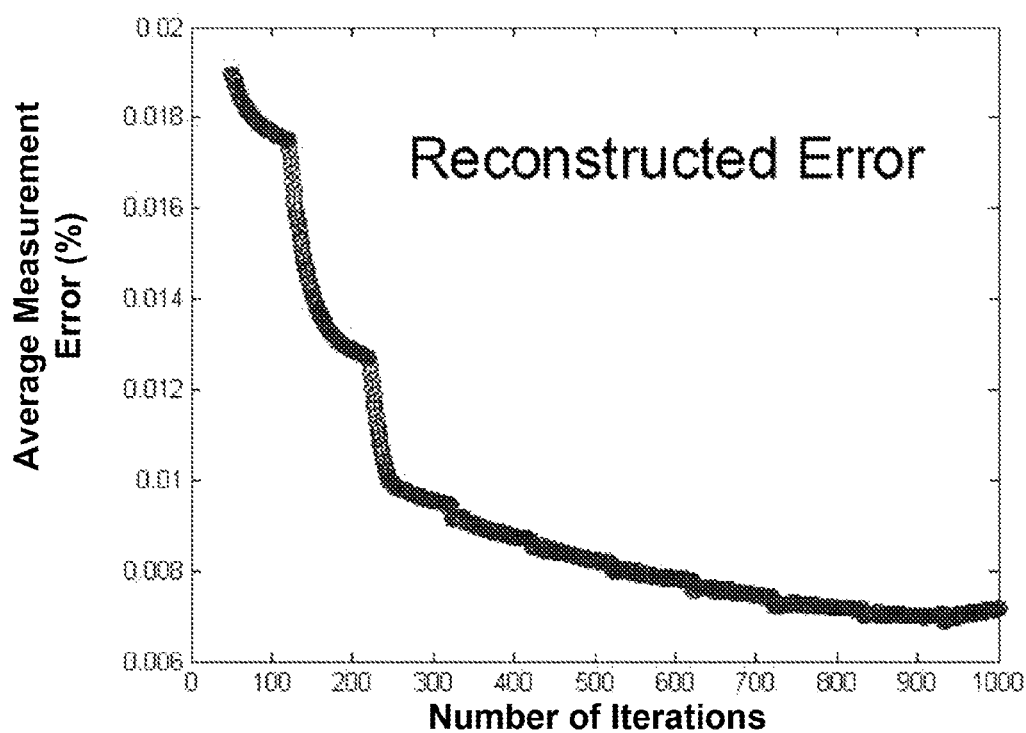
FIG. 9B depicts reconstructed magnetic signal error according to various embodiments of the invention.
Figure 9C:
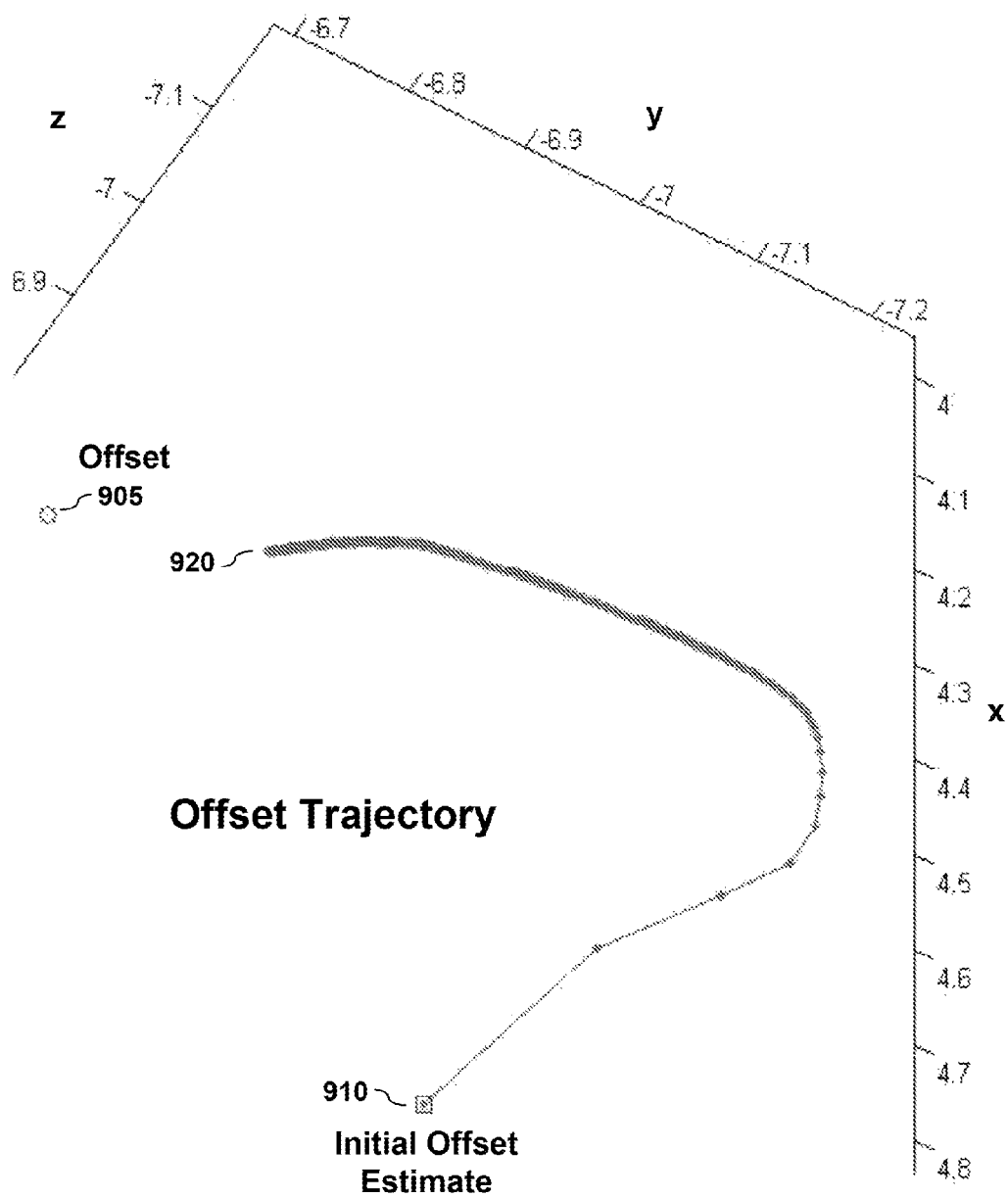
FIG. 9C depicts the trajectory of the offset during the iterations according to various embodiments of the invention.

FIGS. 9A-C shows the estimated current source error (FIG. 9A) and reconstructed magnetic signal error (FIG. 9B). FIG. 9 depicts the initial offset estimate 910 and the trajectory of the offset along each iteration toward the true offset 905. It can be seen that the error decreases significantly within the first several iterations since the temperature parameter is high. When the temperature parameter becomes low, the method steps more cautiously. The offset trajectory may have some jittering or big steps at the beginning due to the high parameter value, but the offset trajectory will become more consistent after the parameter is lowered.

C. One-Dimensional Sensors

The preceding embodiments were configured for sensors that produce three-dimensional measurements. It should be noted that these methods could be applied to other types of sensors, such as one-dimensional sensors. If the same numbers of one-dimensional sensors in a sensor array are used as compared to an array of three-dimensional sensors, there are fewer constraints. Consider Equation (5) (above), each one-dimensional measurement $\vec{B}_m^i$ is dependent on two components of the current vector $\vec{J}_n$. In other words, it is possible to use one-dimensional measurements to recover the three-dimensional current vectors, but to do so involves more sensors and appropriate arrangement of sensors. In embodiments, appropriate arrangement assures enough constraints, such as, for example, not having the sensors arranged in a line.

To use one-dimensional sensors, some of the sensors measure the "x" component of the magnetic field, some measure the "y" component, and others measure the "z" component. Thus, Equation (6) (above) can be rewritten as individual equations:

$$[B_{m_x}^x] = [0 \quad R_{m_x 1}^3 \quad -R_{m_x 1}^2 \quad |...| \quad 0 \quad R_{m_x N}^3 \quad -R_{m_x N}^2] \begin{bmatrix} J_1^1 \\ J_1^2 \\ J^{31} \\ \vdots \\ J_N^1 \\ J_N^2 \\ J_N^3 \end{bmatrix}$$

$$[B_{m_y}^y] = [-R_{m_y 1}^3 \quad 0 \quad R_{m_y 1}^1 \quad |...| \quad R_{m_y N}^3 \quad 0 \quad R_{m_y N}^1] \begin{bmatrix} J_1^1 \\ J_1^2 \\ J^{31} \\ \vdots \\ J_N^1 \\ J_N^2 \\ J_N^3 \end{bmatrix}$$

$$[B_{m_z}^z] = [R_{m_z 1}^2 \quad -R_{m_x 1}^1 \quad 0 \quad |...| \quad R_{m_z N}^2 \quad -R_{m_z N}^1 \quad 0] \begin{bmatrix} J_1^1 \\ J_1^2 \\ J^{31} \\ \vdots \\ J_N^1 \\ J_N^2 \\ J_N^3 \end{bmatrix}$$

where $B_m^x$, is the $m_x^{th}$ sensor that measures the "x" component of the magnetic vector and there are $M^x$ sensors; $B_{m_y}^y$ is the $m_y^{th}$ sensor that measures the "y" component of the magnetic vector and there are $M^y$ sensors; $B^z_{m_z}$ is the $m_z^{th}$ sensor that measures the "z" component of the magnetic vector and there are $M^z$ sensors; and $M=M^x+M^y+M^z$. Accordingly, Equation (7) (above) can be changed to the following:

$$\underbrace{\begin{bmatrix} B_1^x \\ B_2^x \\ \vdots \\ B_{M^x}^x \\ - \\ B_1^y \\ B_2^y \\ \vdots \\ B_{M^y}^y \\ - \\ B_1^z \\ B_2^z \\ \vdots \\ B_{M^z}^z \end{bmatrix}}_{B} = \underbrace{\begin{bmatrix} 0 & R_{11}^3 & -R_{11}^2 & |\ldots| & 0 & R_{1N}^3 & -R_{1N}^2 \\ 0 & R_{21}^3 & -R_{21}^2 & |\ldots| & 0 & R_{2N}^3 & -R_{2N}^2 \\ & \vdots & & |\ldots| & & \vdots & \\ 0 & R_{M^x1}^3 & -R_{M^x1}^2 & |\ldots| & 0 & R_{M^xN}^3 & -R_{M^xN}^2 \\ - & - & - & |\ldots| & - & - & - \\ -R_{11}^3 & 0 & R_{11}^1 & |\ldots| & -R_{1N}^3 & 0 & R_{1N}^1 \\ -R_{21}^3 & 0 & R_{21}^1 & |\ldots| & -R_{2N}^3 & 0 & R_{2N}^1 \\ & \vdots & & |\ldots| & & \vdots & \\ -R_{M^y1}^3 & 0 & R_{M^y1}^1 & |\ldots| & -R_{M^yN}^3 & 0 & R_{M^yN}^1 \\ - & - & - & |\ldots| & - & - & - \\ R_{11}^2 & -R_{11}^1 & 0 & |\ldots| & R_{1N}^2 & -R_{1N}^1 & 0 \\ R_{21}^2 & -R_{21}^1 & 0 & |\ldots| & R_{2N}^2 & -R_{2N}^1 & 0 \\ & \vdots & & |\ldots| & & \vdots & \\ R_{M^z1}^2 & -R_{M^z1}^1 & 0 & |\ldots| & R_{M^zN}^2 & -R_{M^zN}^1 & 0 \end{bmatrix}}_{R'} \underbrace{\begin{bmatrix} J_1^1 \\ J_1^2 \\ J_1^3 \\ \vdots \\ J_N^1 \\ J_N^2 \\ J_N^3 \end{bmatrix}}_{J}$$

where B' is an M×1 vector, R' is an M×3N matrix, and J is a 3N×1 vector. When rank(R')≧3N, a least square solution for J can be obtained:

$$J=(R'^T R')^{-1} R'^T B' \qquad (8')$$

Equation 12 (above) can also be adapted as follows:

$$\left. \begin{aligned} f_{m_x}^x(x,y,z) &= -\alpha B_{m_x}^x + \sum_{n=1}^{N} \frac{-J_n^3 y + J_n^2 z + \tau_{m_x n}^1}{((x+\gamma_{m_x n}^1)^2 + (y+\gamma_{m_x n}^2)^2 + (z+\gamma_{m_x n}^3)^2)^{3/2}} = 0 \\ f_{m_y}^y(x,y,z) &= -\alpha B_{m_y}^y + \sum_{n=1}^{N} \frac{-J_n^3 x + J_n^1 z + \tau_{m_y n}^2}{((x+\gamma_{m_y n}^1)^2 + (y+\gamma_{m_y n}^2)^2 + (z+\gamma_{m_y n}^3)^2)^{3/2}} = 0 \\ f_{m_z}^z(x,y,z) &= -\alpha B_{m_z}^z + \sum_{n=1}^{N} \frac{-J_n^2 x + J_n^1 y + \tau_{m_z n}^3}{((x+\gamma_{m_z n}^1)^2 + (y+\gamma_{m_z n}^2)^2 + (z+\gamma_{m_z n}^3)^2)^{3/2}} = 0 \end{aligned} \right\} \qquad (12')$$

Let $F^x=(f_1^x, f_2^x, \ldots, f_{M^x}^x)^T=0$, $F^y=(f_1^y, f_2^y, \ldots, f_{M^y}^y)^T=0$, and $F^z=(f_1^z, f_2^z, \ldots, f_{M^z}^z)^T=0$ and $F'=(F^{xT}, F^{yT}, F^{zT})^T=0$. Then nonlinear system F' can be solved to obtain a least square solution of the nonlinear system F'.

One skilled in the art shall recognize that the preceding methods for obtaining the electrical current values described with respect to three-dimensional sensors may also be adapted for one-dimensional sensor configurations. Consider, by way of example and not limitation, the method depicted in FIG. 10.

Figure 10:
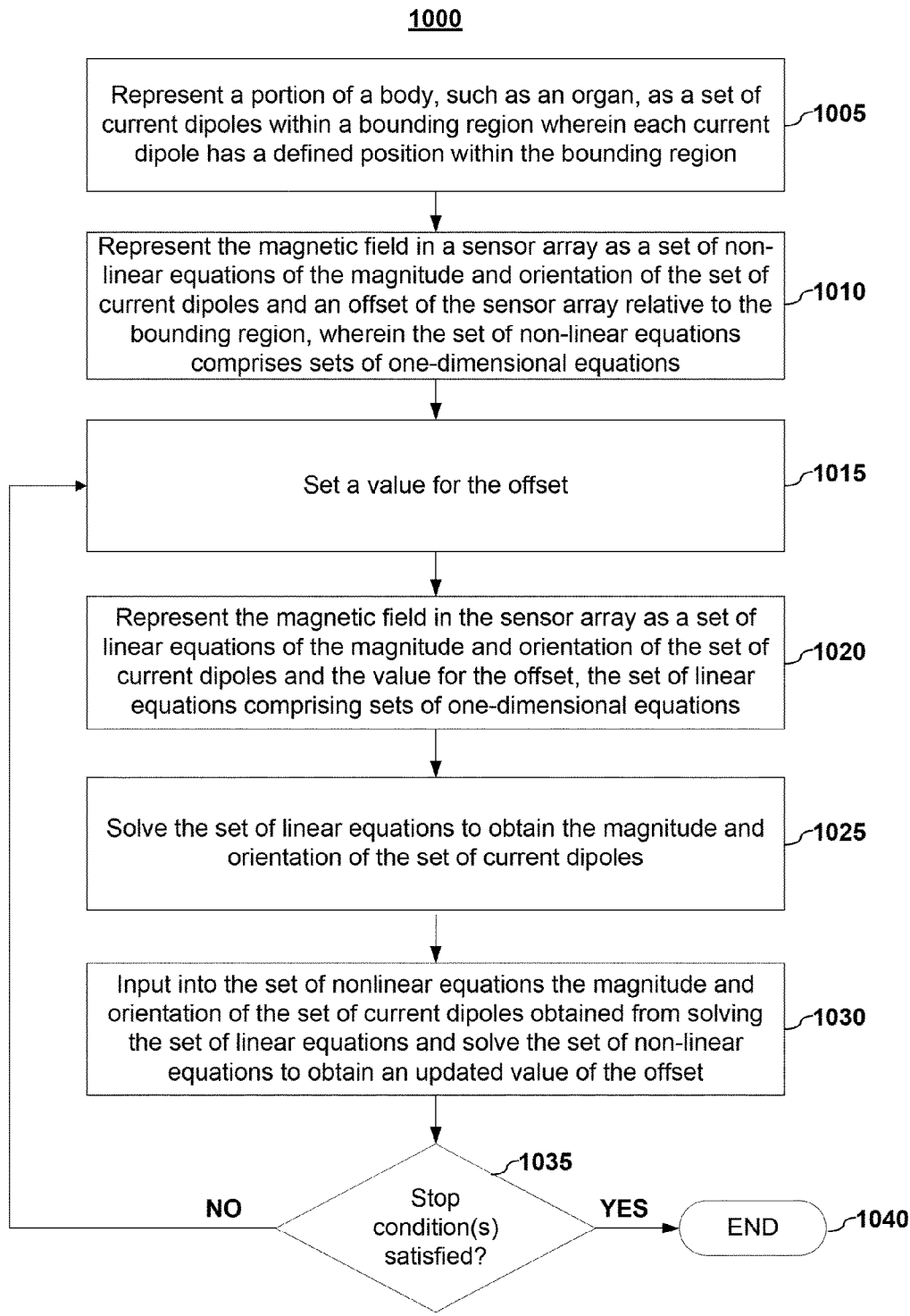
FIG. 10 depicts a method for reconstructing electrical current distribution of an organ using one-dimensional sensors according to various embodiments of the invention.

FIG. 10 depicts a method for reconstructing electrical current distribution of an organ using one-dimensional sensors according to various embodiments of the invention. One skilled in the art shall recognize that the method 1000 depicted in FIG. 10 is analogous to the method 600 depicted in FIG. 6.

As with the prior methods, the body part of interest is represented (1005) as a set of current dipoles within a bounding region wherein each current dipole has a defined position within the bounding region. And, the magnetic field at a sensor array is represented (1010) as a set of nonlinear equations of the magnitude and orientation of the set of current dipoles and an offset of the sensor array relative to the bounding region, wherein the set of nonlinear equations comprises sets of one-dimensional equations, such as Equation (12') (above). A value for the offset is selected (1015). In embodiments, the initial value for the offset may be an estimate. The estimate may be based upon statistical data of anatomy, measurements taken of the patient, measurements of the equipment configuration, measurements of the set-up, or combinations thereof.

As was noted previously, the magnetic field in the sensor array can be represented (1020) as a set of linear equations of the magnitude and orientation of the set of current dipoles and the value for the offset, wherein the set of linear equations comprise sets of one-dimensional equations. For example, Equation (8') sets forth a linear system to obtain the current source, J. Thus, the set of linear equations can be solved (1025) to obtain the magnitude and orientation of the set of current dipoles. Equation (8') sets forth a least squared solution to the linear system.

The magnitude and orientation of the set of current dipoles obtained from the set of linear equations can be inputted (1030) into the set of nonlinear equations. The set of nonlinear equations can be solved to obtain an update value of the offset. In embodiments, a Levenberg-Marquardt methodology is used to solve the nonlinear system.

In embodiments, if a stop condition is satisfied (1035), the method stops (1040). The stop conditions may be the same or similar to those listed with respect to method 600. If a stop condition has not been satisfied (1035), the method iterates in which the update value of the offset is used to update the offset for the next iteration (Step 1015). That is, once an offset ($\vec{\epsilon}_0$) is obtained, the position of the sensors can be estimated and J can be computed again. This process is iterated until the algorithm converges, or some other stop condition is satisfied.

As noted previously, one skilled in the art shall recognize that the other methods for obtaining the current values described with respect to three-dimensional sensors may also be applied to one-dimensional sensor configurations.

D. Multi-Scale Embodiments

To improve the initial estimate for the iterative methods discussed above, a multi-scale strategy may be employed to solve the offset from coarse to fine. In embodiments, an octree structure system may be employed, although one skilled in the art shall recognize that other multi-scale configurations may be employed.

1. General Multi-Scale Embodiments

Figure 11:
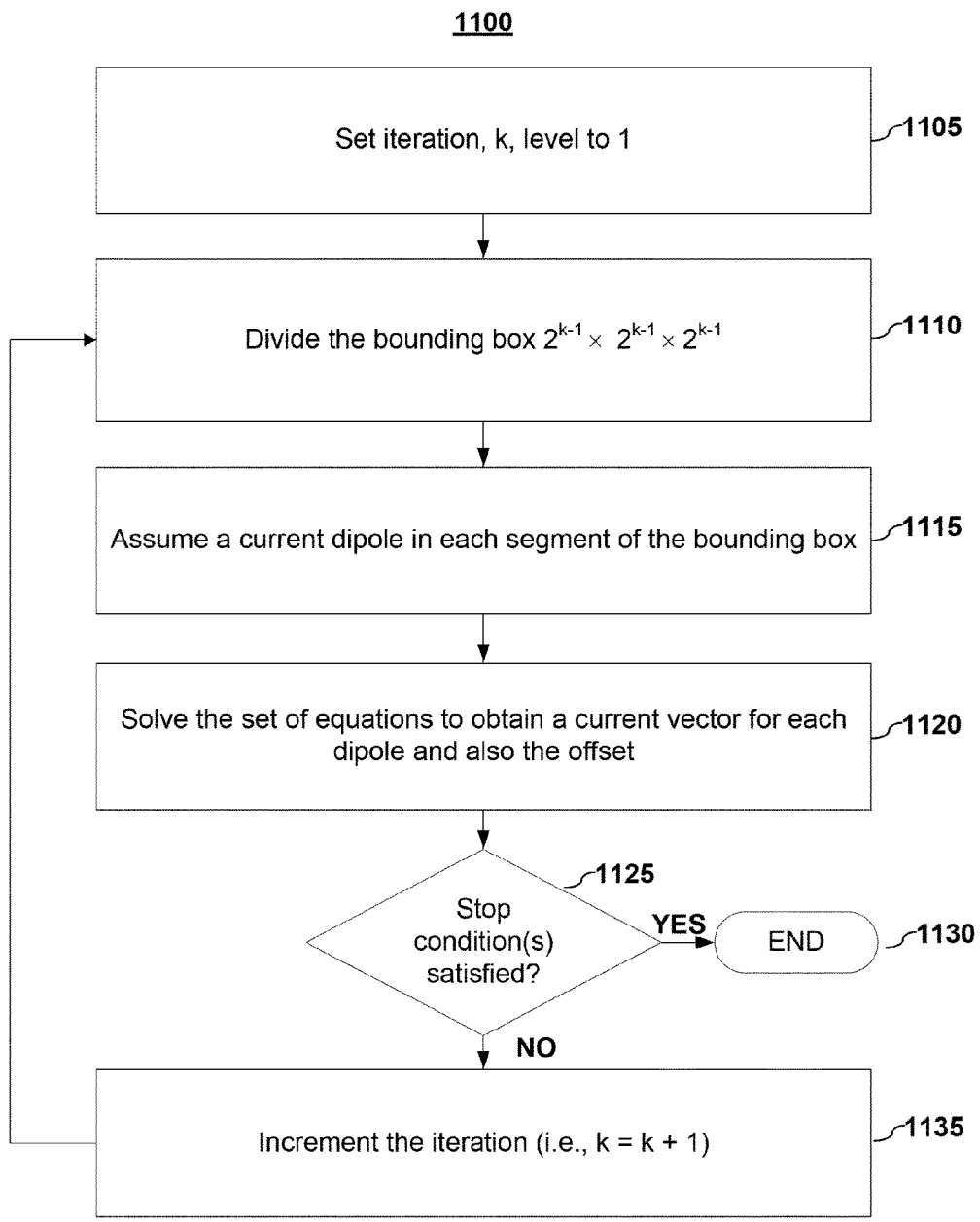
FIG. 11 depicts a method for reconstructing electrical current distribution of an organ using a multi-scale strategy according to various embodiments of the invention.

FIG. 11 depicts a method for reconstructing electrical current distribution of an organ using a multi-scale strategy according to various embodiments of the invention. At the very beginning, the method initializes (1105) the level to level 1. In any level k, the bounding box is divided (1110) into a $2^{k-1} \times 2^{k-1} \times 2^{k-1}$ dipole array. Thus, at level 1, it is assumed (1115) that there is only one current dipole and that it is located at the origin of the world or global coordinates. In this embodiment, a dipole is assumed (1115) to be at the center of a divided bounding region, but one skilled in the art shall recognize that other dipole placement may be used. The current vector is obtained at that dipole and also the offset (see, for example, step 620-630 or 1020-1030). If a stop condition has not been reached (1125), the level increments (1140) and the process repeats by returning to step 1110. For example, at level 2, the bounding box is divided into a 2×2×2 dipole array, the updated offset that was just obtained is used as the estimated, and the method is repeated. The stop conditions can be the same or similar to those discussed previous. An additional stop condition may be when the rank(R) is equal to 3N, since the rank(R) must be greater than or equal to 3N. One skilled in the art shall recognize that the check for stop conditions may be skipped for the first (or more) iterations.

2. Multi-Scale Embodiments to Improve Source Resolution

In addition to helping improve the offset estimate, a multi-scale strategy can also improve the source resolution. As noted above, the number of sources cannot exceed the number of the sensors (that is, rank(R) must be greater than or equal to 3N), which limits the resolution of the elementary source array. One way to improve the source resolution is to increase the number of the sensors. Another way to improve the resolution is to change the representation of the source array. By using a dynamic allocation of source arrays in connection with the multi-scale framework, the source resolution can be increased. In embodiments, it is assumed that in the multi-scale framework, level k, if the estimated magnitude of any dipole is too small to be counted, then in the next level (k+1), this dipole/node will be disregarded and will not generate sub-nodes. Consider, by way of illustration, the method 1200 depicted in FIG. 12.

Figure 12:
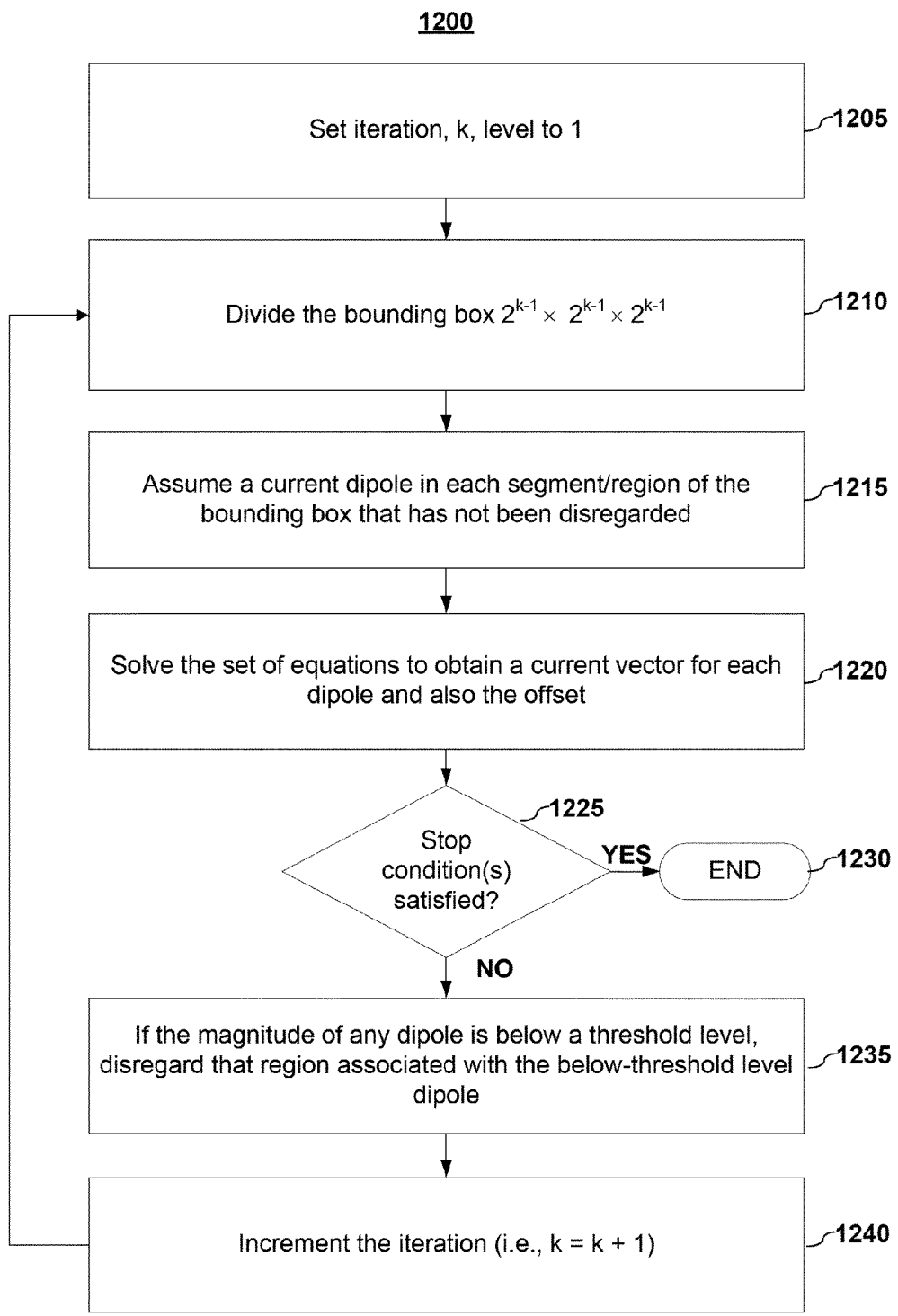
FIG. 12 depicts an alternative method for reconstructing electrical current distribution of an organ using a multi-scale strategy according to various embodiments of the invention.
Figure 13:
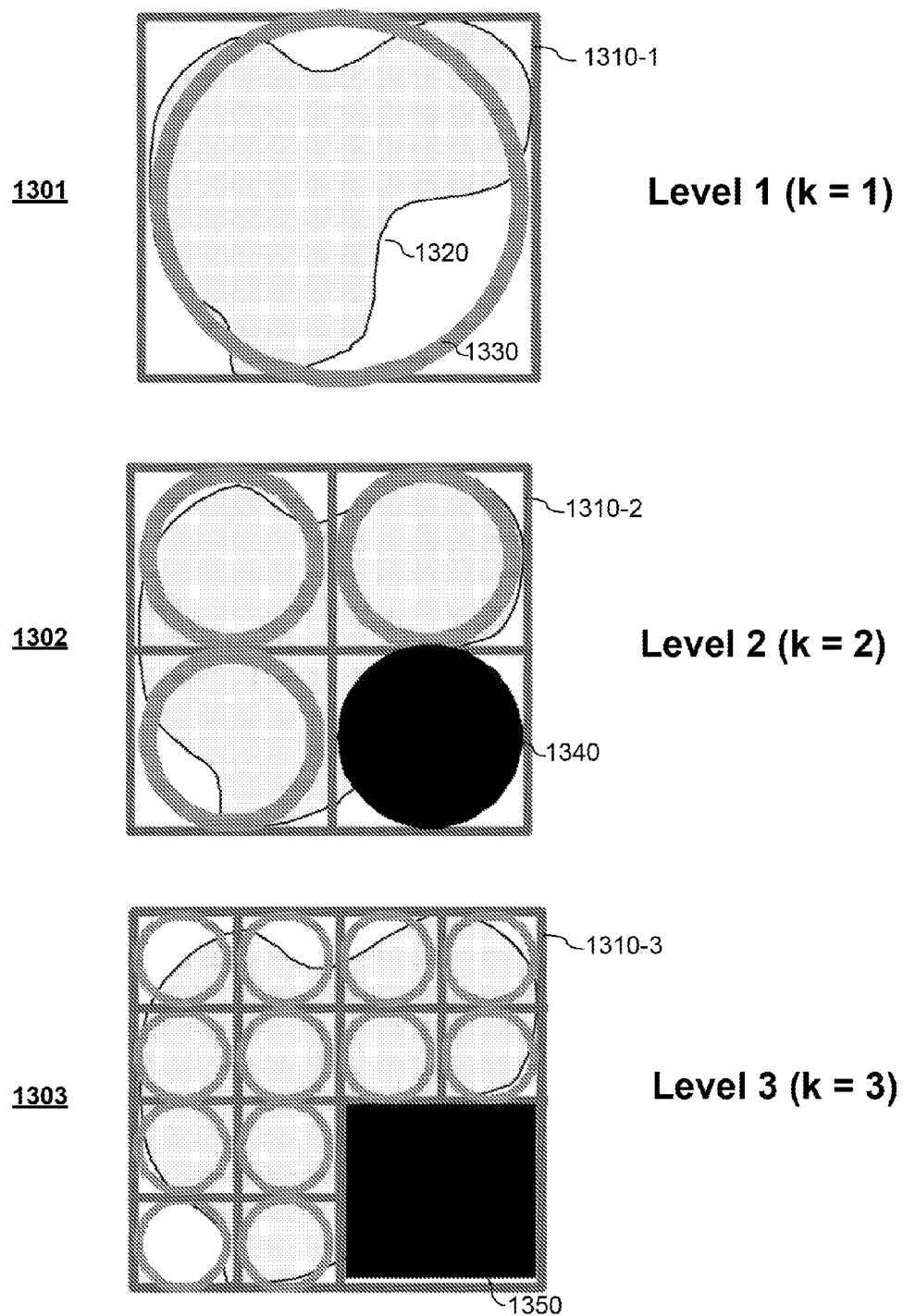
FIG. 13 depicts an example of different levels of a multi-scale strategy according to various embodiments of the invention.

FIG. 12 depicts an alternative method for reconstructing electrical current distribution of an organ using a multi-scale strategy according to various embodiments of the invention. At the very beginning, the method initializes (1205) the level to level 1. At a level k, the bounding box is divided (1210) into a $2^{k-1} \times 2^{k-1} \times 2^{k-1}$ dipole array. Thus, at level 1, it is assumed (1215) that there is only one current dipole and that it is located at the origin of the world or global coordinates. As mentioned previously, the positioning of a dipole is a matter of implementation and not critical to the present invention. FIG. 13 depicts an example of cross-sections of a portion of a bounding region at different levels of a multi-scale strategy according to various embodiments of the invention. At level 1, there is one bounding region 1310-1 with a single dipole 1330. The active region of the organ is also depicted 1320.

As explained with respect to method 1100, the current vector is obtained at that dipole and also the offset (see, for example, step 620-630 or 1020-1030). If a stop condition has not been reached (1225), the magnitude of the current is examined. If the magnitude of a dipole is below a threshold value, the region associated with that dipole is disregarded. One skilled in the art shall recognize that the check for stop conditions and the examination of the magnitude may be skipped for the first (or more) iterations.

The level increments (1240), and the process repeats by returning to step 1210. For example, at level 2, the bounding box is divided into a 2×2×2 dipole array. Cross-section 1302 depicts the subdivided segments or regions at level 2. Note that the bounding region 1310-2 contains four sub-bounding regions, each with its own current dipole. Using the offset that was just obtained, the method is repeated to obtain the new current values. Upon examination, it is determined that one of the dipoles, 1340, has a magnitude that is below a threshold value. In embodiments, the threshold value may be obtained by examining the magnitude values of the some or all of the dipoles. For example, a dipole with a value that is below a certain percentile, such as 10%, of the second smallest dipole current value may be disregarded. Alternatively, or additionally, the threshold value may be based upon prior experience and/or other statistical measures. Since the dipole 1340 was disregarded, in the next iteration, that region is not segmented. Consider, by way of illustration, the level 3 cross-section 1303 of FIG. 13. The region 1350 associated with the disregarded dipole 1340 was not subdivided, while the other regions were subdivided to form bounding regions 1310-3. By disregarding regions of no or low current dipole, the other regions can have more dipoles thereby increasing the source resolution.

The process is iterated until a stop condition is satisfied (1225). It should be noted that the stop conditions may be the same or similar to those discussed with respect to the prior multi-scale method (method 1100).

E. System Implementations

In embodiments, a computing system may be configured to perform one or more of the methods presented herein. Systems that implement at least one or more of the methods described herein may comprise a current-from-magnetic-data application operating on a computer system that interfaces with or receives data from (directly and/or indirectly) one or more sensor arrays. The computer system may comprise one or more computers and one or more databases. In embodiments, the current-from-magnetic-data application may be part of diagnostic equipment or may be a standalone device. In embodiments, the computer system may use the electrical current dipole information to model the portion of the body and may be graphically depicted it. In embodiments, the computer system may use the electrical current dipole information to assist in diagnosis and/or treatment.

It shall be noted that the present invention may be implemented in any instruction-execution/computing device or system capable of processing image data, including without limitation, a general-purpose computer and a specific computer, such as one intended for data or image processing. It shall be noted that aspects of the present invention may also be implemented into other computing devices and systems, including without limitation, a digital camera, a projector, a multimedia device, and any other device that projects, processes, captures, transmits, or stores an image. Furthermore, within any of the devices, aspects of the present invention may be implemented in a wide variety of ways including software, hardware, firmware, or combinations thereof. For example, the functions to practice various aspects of the present invention may be performed by components that are implemented in a wide variety of ways including discrete logic components, one or more application specific integrated circuits (ASICs), and/or program-controlled processors. It shall be noted that the manner in which these items are implemented is not critical to the present invention.

Figure 14:
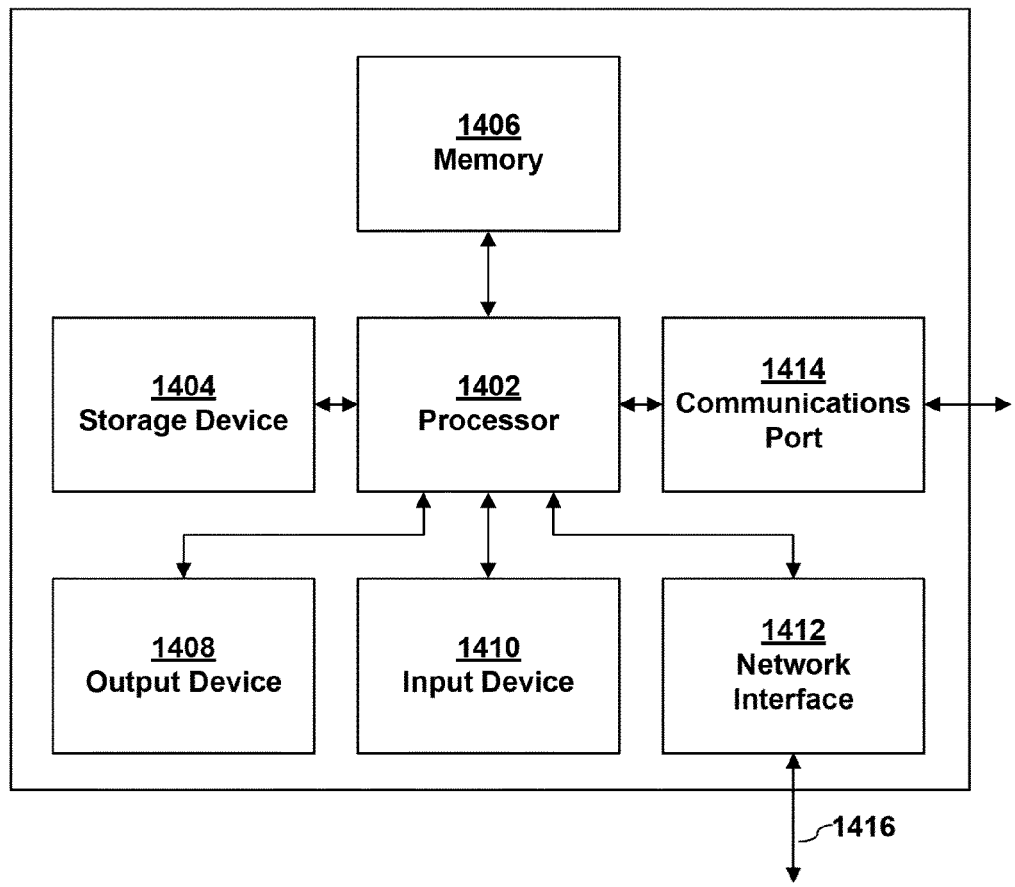
FIG. 14 depicts a computing system according to various embodiments of the invention.

FIG. 14 depicts a functional block diagram of an embodiment of an instruction-execution/computing device 1400 that may implement or embody embodiments of the present invention. As illustrated in FIG. 14, a processor 1402 executes software instructions and interacts with other system components. In an embodiment, processor 1402 may be a general purpose processor such as (by way of example and not limitation) an AMD processor, an INTEL processor, a SUN MICROSYSTEMS processor, or a POWERPC compatible-CPU, or the processor may be an application specific processor or processors. A storage device 1404, coupled to processor 1402, provides long-term storage of data and software programs. Storage device 1404 may be a hard disk drive and/or another device capable of storing data, such as a computer-readable media (e.g., diskettes, tapes, compact disk, DVD, and the like) drive or a solid-state memory device. Storage device 1404 may hold programs, instructions, and/or data for use with processor 1402. In an embodiment, programs or instructions stored on or loaded from storage device 1404 may be loaded into memory 1406 and executed by processor 1402. In an embodiment, storage device 1404 holds programs or instructions for implementing an operating system on processor 1402. In one embodiment, possible operating systems include, but are not limited to, UNIX, AIX, LINUX, Microsoft Windows, and the Apple MAC OS. In embodiments, the operating system executes on, and controls the operation of, the computing system 1400.

An addressable memory 1406, coupled to processor 1402, may be used to store data and software instructions to be executed by processor 1402. Memory 1406 may be, for example, firmware, read only memory (ROM), flash memory, non-volatile random access memory (NVRAM), random access memory (RAM), or any combination thereof. In one embodiment, memory 1406 stores a number of software objects, otherwise known as services, utilities, components, or modules. One skilled in the art will also recognize that storage 1404 and memory 1406 may be the same items and function in both capacities. In an embodiment, one or more of the methods depicted herein may be embodied in one or more modules stored in a computer readable media, such as memory 1404, 1406, and executed by processor 1402.

In an embodiment, computing system 1400 provides the ability to communicate with other devices, other networks, or both. Computing system 1400 may include one or more network interfaces or adapters 1412, 1414 to communicatively couple computing system 1400 to other networks and devices. For example, computing system 1400 may include a network interface 1412, a communications port 1414, or both, each of which are communicatively coupled to processor 1402, and which may be used to couple computing system 1400 to other computer systems, networks, and devices.

In an embodiment, computing system 1400 may include one or more output devices 1408, coupled to processor 1402, to facilitate displaying graphics and text. Output devices 1408 may include, but are not limited to, a display, LCD screen, CRT monitor, printer, touch screen, or other device for displaying information. In embodiments, the dipole information may be used to graphically depict the body part under examination. In embodiments, the body part as part of a model of the body part and may also depict the body part at various time intervals. Computing system 1400 may also include a graphics adapter (not shown) to assist in displaying information or images on output device 1408.

One or more input devices 1410, coupled to processor 1402, may be used to facilitate user input. Input device 1410 may include, but are not limited to, a pointing device, such as a mouse, trackball, or touchpad, and may also include a keyboard or keypad to input data or instructions into computing system 1400.

In an embodiment, computing system 1400 may receive input, whether through communications port 1414, network interface 1412, stored data in memory 1404/1406, or through an input device 1410, from a scanner, copier, facsimile machine, diagnostic equipments, sensors, or other computing device.

One skilled in the art will recognize no computing system is critical to the practice of the present invention. One skilled in the art will also recognize that a number of the elements described above may be physically and/or functionally separated into sub-modules or combined together.

It shall be noted that embodiments of the present invention may further relate to computer products with a computer-readable medium that have computer code thereon for performing various computer-implemented operations. The media and computer code may be those specially designed and constructed for the purposes of the present invention, or they may be of the kind known or available to those having skill in the relevant arts. Examples of computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present invention may be implemented in whole or in part as machine-executable instructions that may be in program modules that are executed by a computer. Examples of program modules include libraries, programs, routines, objects, components, and data structures. In distributed computing environments, program modules may be physically located in settings that are local, remote, or both.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A computer program product comprising at least one non-transitory computer-readable medium storing one or more sequences of instructions, wherein execution of the one or more sequences of instructions by one or more processors causes the one or more processors to execute a computer-implemented method for reconstructing electrical current distribution of a portion of a body, the method comprising:

[a] representing the portion of the body as a set of electrical current dipoles with a fixed positional relationship to each other within a bounding region, each electrical current dipole having a defined fixed positional relationship to a current dipole origin point within the bounding region;

[b] representing a magnetic field in a sensor array as a set of nonlinear equations of the magnitude and orientation of the set of electrical current dipoles, said sensor array having a defined array origin point within a bounding region of said sensor array, and said magnetic field being further represented by an offset from he defined array origin point to the current dipole origin point within the bounding region;

[c] setting a value for the offset;

[d] representing the magnetic field in the sensor array as a set of linear equations of the magnitude and orientation of the set of electrical current dipoles and the value for the offset;

[e] solving the set of linear equations to obtain the magnitude and orientation of the set of electrical current dipoles;

[f] inputting into the set of nonlinear equations the magnitude and orientation of the set of electrical current dipoles obtained from solving the set of linear equations and solving the set of nonlinear equations to obtain an updated offset; and

[g] IF a stop condition is not met, THEN using the updated offset as the value for the offset and returning to step [d]; ELSE defining the current set of electrical current dipoles at their current position as the reconstructed electrical current distribution of the portion of the body.

2. The computer program product of claim 1 wherein the step of solving the set of nonlinear equations to obtain an updated offset comprises:

solving the set of nonlinear equations to obtain an update value and adjusting the offset using the update value to obtain the updated offset.

3. The computer program product of claim 2 wherein the step of solving the set of nonlinear equations to obtain an update value comprises:

as part of an iterative optimization to solve the set of nonlinear equations, multiplying the update value by a parameter and adding that product to the offset to obtain an updated offset to use for the next iteration of the iterative optimization.

4. The computer program product of claim 3 wherein the parameter is part of a simulated annealing.

5. The computer program product of claim 1 wherein the set of nonlinear equations comprises sets of one-dimensional equations and the set of linear equations comprises sets of one-dimensional equations.

6. The computer program product of claim 1 wherein a stop condition is at least one of the following:

a difference between the offset and the updated offset is less than a threshold value;

a number of iterations have occurred;

a difference between the offset and the updated offset is increasing relative to a difference of prior iterations; and a measurement reconstruction error is less than a threshold amount.

7. The computer program product of claim 1 further comprising the step of:

[h] graphically depicting the electrical current dipoles.

8. A computer program product comprising at least one non-transitory computer-readable medium storing one or more sequences of instructions, wherein execution of the one or more sequences of instructions by one or more processors causes the one or more processors to execute a computer-implemented method for reconstructing electrical current distribution of a portion of a body, the method comprising:

[a] setting a value for the offset;

[b] representing the portion of the body as a set of electrical current dipoles with a fixed positional relationship to each other within a bounding region, each electrical current dipole having a predefined fixed positional relationship to a current dipole origin point within the bounding region;

[c] representing a magnetic field in a sensor array as a set of nonlinear equations of the magnitude and orientation of the set of electrical current dipoles, said sensor array having a defined array origin point within a bounding region of said sensor array, and said magnetic field being further represented by an offset from the defined array origin point to the current dipole origin point within the bounding region;

[d] representing the magnetic field in the sensor array as a set of linear equations of the magnitude and orientation of the set of electrical current dipoles and the value for the offset;

[e] solving the set of linear equations to obtain the magnitude and orientation of the set of electrical current dipoles;

[f] inputting into the set of nonlinear equations the magnitude and orientation of the set of electrical current dipoles obtained from solving the set of linear equations and solving the set of nonlinear equations to obtain an updated offset; and

[g] if a stop condition is not met, then using the updated offset as the value for the offset; increasing the number of remaining current dipoles by subdividing at least some of the electrical current dipoles regions; and returning to step [b]; else defining the current set of electrical current dipoles at their current position as the reconstructed electrical current distribution of the portion of the body.

9. The computer program product of claim 8 wherein step of increasing the number of remaining current dipoles by subdividing at least some of the current dipoles regions comprises:

responsive to the magnitude of a electric current dipole having a value below a threshold, disregarding the electric current dipole and its associated region within the bounding region; and increasing the number of remaining current dipoles by subdividing at least some of the non-disregarded electric current dipoles regions.

10. The computer program product of claim 8 wherein the set of nonlinear equations comprises sets of one-dimensional equations and the set of linear equations comprises sets of one-dimensional equations.

11. The computer program product of claim 8 wherein a stop condition is that another subdivision would result in the number of current dipoles exceeding a threshold value related to the number of sensors in the sensor array.

12. The computer program product of claim 8 further comprising:

using a parameter in conjunction with the Levenberg-Marquardt method to obtain the updated offset, wherein the parameter is multiplied with an update offset value in at least some iterations of the Levenberg-Marquardt method and the updated offset is a sum of the current offset and the product of the parameter multiplied with the update offset value.

13. A computer system for obtaining current information from magnetic data, the system comprising:
one or more processors; and
one or more non-transitory computer readable media in communication with the one or more processors, the computer readable medium having stored thereon a set of instructions executable by the one or more processors, set of instructions comprising:
[a] representing a portion of a body as a set of electrical current dipoles with a fixed positional relationship to each other within a bounding region, each electrical current dipole having a defined positional relationship to a current dipole origin point within the bounding region;
[b] representing a magnetic field in a sensor array as a set of nonlinear equations of the magnitude and orientation of the set of electrical current dipoles, said sensor array having a defined array origin point within a bounding region of said sensor array, and an offset from the defined array origin point to the current dipole origin point within the bounding region;
[c] setting a value for the offset;
[d] representing the magnetic field in the sensor array as a set of linear equations of the magnitude and orientation of the set of electrical current dipoles and the value for the offset;
[e] solving the set of linear equations to obtain the magnitude and orientation of the set of electrical current dipoles;
[f] inputting into the set of nonlinear equations the magnitude and orientation of the set of electrical current dipoles obtained from solving the set of linear equations and solving the set of nonlinear equations to obtain an updated offset; and
[g] If to a stop condition is not met, THEN using the updated offset as the value for the offset and returning to step [d];
ELSE defining the current set of electrical current dipoles at their current position as the reconstructed electrical current distribution of the portion of the body.

14. The system of claim 13 wherein the step of solving the set of nonlinear equations to obtain an updated offset comprises:
solving the set of nonlinear equations to obtain an update value and adjusting the offset using the update value to obtain the updated offset.

15. The system of claim 14 wherein the step of adjusting the offset using the update value to obtain the updated offset comprises:
multiplying the update value by a parameter and adding that product to the offset to obtain the updated offset.

16. The system of claim 13 wherein the set of nonlinear equations comprises sets of one-dimensional equations and the set of linear equations comprises sets of one-dimensional equations.

17. The system of claim 13 wherein a stop condition is at least one of the following:
a difference between the offset and the updated offset is less than a threshold value;
a number of iterations have occurred;
a difference between the offset and the updated offset is increasing relative to a difference of prior iterations; and
a measurement reconstruction error is less than a threshold amount.

18. The system of claim 13 further comprising a display and the one or more computer readable media further comprising a set of instructions for graphically depicting the electrical current dipoles.

19. The computer program product of claim 1, wherein said bounding region is a moveable three-dimensional volume of fixed shape defined by the distribution of said set of electrical current dipoles and the position of said current dipole origin point.

20. The system of claim 13, wherein said wherein said bounding region is a moveable three-dimensional volume of fixed shape defined by the distribution of said set of electrical current dipoles and the position of said current dipole origin point.

* * * * *